(12) United States Patent
Knochel et al.

(10) Patent No.: US 9,334,237 B2
(45) Date of Patent: May 10, 2016

(54) PRODUCTION AND USE OF ZINC AMIDES

(75) Inventors: Paul Knochel, München (DE); Marc Mosrin, München (DE)

(73) Assignee: Ludwig-Maximilians-Universitat Munchen (DE)

( * ) Notice: Subject to any disclaimer, the term of this patent is extended or adjusted under 35 U.S.C. 154(b) by 0 days.

(21) Appl. No.: 13/147,339

(22) PCT Filed: Feb. 11, 2010

(86) PCT No.: PCT/EP2010/051677
§ 371 (c)(1),
(2), (4) Date: Aug. 3, 2011

(87) PCT Pub. No.: WO2010/092096
PCT Pub. Date: Aug. 19, 2010

(65) Prior Publication Data
US 2011/0288296 A1 Nov. 24, 2011

(30) Foreign Application Priority Data

Feb. 13, 2009 (EP) .................... 09100112

(51) Int. Cl.
C07D 211/10 (2006.01)
C07F 3/00 (2006.01)
(52) U.S. Cl.
CPC .............. *C07D 211/10* (2013.01); *C07F 3/003* (2013.01)
(58) Field of Classification Search
CPC .................................................. C07D 211/10
USPC ...................................................... 546/346
See application file for complete search history.

(56) References Cited

U.S. PATENT DOCUMENTS 8,134,005 B2 3/2012 Knochel et al.
2010/0160632 A1* 6/2010 Knochel et al. ................. 546/11

FOREIGN PATENT DOCUMENTS

JP 2004 010585 A 1/2004

OTHER PUBLICATIONS

Andrikopoulos, et al. "Selective *Meta*-Deprotonation of Toluene by Using Alkali-Metal-Mediated Magnesiation", *Angew. Chem. Int.* 44 (2005), pp. 3459-3462.
Armstrong, et al. "Directed *meta*-Metalation Using Alkali-Metal-Mediated Zincation", *Angew. Chem. Int.* 45 (2006), pp. 3775-3778.
Awad, et al. "Deprotonation of fluoro aromatics using lithium magnesates", *Tetrahedron Let.* 45 (2004), pp. 6697-6701.
Bayh, et al. "Deprotonation of Benzoxazole and Oxazole Using Lithium Magnesates", *J. Org. Chem.* 70 (2005), pp. 5190-5196.
Benderitter, et al. "2-Amino-6-iodo-4-tosyloxypyrimidine: a versatile key intermediate for regioselective functionalization of 2-aminopyrimidines in 4- and 6-positions", *Tetrahedron* 63 (2007), pp. 12465-12470.
Boudet, et al. "Oxidative Amination of Cuprated Pyrimidine and Purine Derivatives", *Organic Let.* 10 (2008), No. 9, pp. 1715-1718.
Clayden, et al. "Contra-Friedel-Crafts *tert*-butylation of substituted aromatic rings via directed metallation and sulfinylation", *Chem. Commun.* (2006), pp. 1393-1394.
Clegg, et al. "Alkali-Metal-Mediated Zincation of Anisole: Synthesis and Structures of Three Instructive Ortho-Zincated Complexes", *J. Am. Chem. Soc.* 128 (2006), pp. 7434-7435.
Clegg, et al. "Post-Metalation Structural Insights into the Use of Alkali-Metal-Mediated Zincation for Directed *ortho*-Metalation of a Tertiary Aromatic Amide", *Angew. Chem. Int.* 45 (2006), pp. 2374-2377.
Clegg, et al. "Pre-Metalation Structural Insights into the Use of Alkali-Metal-Mediated Zincation for Directed *ortho*-Metalation of a Tertiary Aromatic Amide", *Angew. Chem. Int.* 45 (2006), pp. 2370-2374.
Clososki, et al. "Direct Magnesiation of Polyfunctionalized Arenes and Heteroarenes Using (tmp)$_2$Mg 2LiCl", *Angew. Chem. Int.* 46 (2007), pp. 7681-7684.
Do, et al. "A General Methid for Copper-Catalyzed Arylation of Arene C—H Bonds", *J. Am. Chem. Soc.* 130 (2008), pp. 15185-15192.
Eaton, et al. "Transmetalation and Reverse Transmetalation on Ortho-Activated Aromatic Compounds: A Direct Route to o ,o'-Disubstituted Benzenes", *J. Org. Chem.* 53 (1988), pp. 2728-2732.
Eaton, et al. "Magnesium Amide Bases and Amido-Grignards. 1. Ortho Magnesiation", *J. Am. Chem. Soc.* 111 (1988), pp. 8016-8018.
Eaton, et al. "Through-Space Amide Activation of C—H Bonds in Triangulanes", *J. Am. Chem. Soc.* 115 (1993), pp. 11370-11375.
Eaton, et al. "A New Approach to Substitute Cyclobutanes: Direct β-Deprotonation Magnesiation of Cyclobutane carboxamides", *Synlett* 9 (2003), pp. 1275-1278.
Farkas, et al. "Reactions of Organomagnesates and Aryl Halides: Metalation and Nucleophilic Substitution", *Organomet.* 23 (2004), pp. 432-427.
García-Alvarez, et al. "Unmasking Represebntative Structures of TMP-Active Hauser and Turbo-Hauser Bases", *Angew. Chem. Int.* 47 (2008), pp. 8079-8081.

(Continued)

*Primary Examiner* — Brian McDowell

(57) ABSTRACT

A reagent of the formula

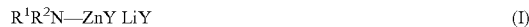

$$R^1R^2N\text{—}ZnY\ LiY \quad (I)$$

wherein $R^1$ and $R^2$ are independently, selected from H, aryl or heteroaryl, linear, branched or cyclic, substituted or unsubstituted alkyl, alkenyl, alkynyl, or silyl derivatives thereof; and $R^1$ and $R^2$ together form part of a cyclic or polymeric structure; $R^1$ and/or $R^2$ is not H; Y is F, Cl, Br, I, CN, SCN, NCO or HalO$_n$, wherein n=3 or 4 and Hal is Cl, Br or I; NO$_3$; BF$_4$; PF$_6$; H; a carboxylate of formula $R^5CO_2$; an alcoholate of formula OR$^5$; a thiolate of formula SR$^5$; $R^5P(O)O_2$; or SCOR$^5$; or SCSR$^5$; O$_n$SR$^5$; wherein n=2 or 3; or NO$_n$, wherein n=2 or 3; and a derivative thereof; wherein $R^5$ is an aryl or heteroaryl, linear, branched or cyclic, alkyl, alkenyl, alkynyl, or derivatives thereof, or H; or as adduct with a solvent; and preparation and use thereof.

1 Claim, No Drawings

(56) References Cited

OTHER PUBLICATIONS

Gong, et al. "Preparation of Highly Functionalized Heterocyclic Zinc Organometallics via a Li(acac)-Catalysis of the I/Zn-Exchange Reaction", *Synlett* 2(2005), pp. 0267-0270.

Hevia, et al. "Trapping, Stabilization, and Characterization of an Enolate Anion of a 1,6-Adduct of Benzophenone Chelated by a Sodium Alkylamidozincate Cation", *J. Am. Chem. Soc.* 127 (2005), pp. 13106-13107.

Hevia, et al. "Synergic Monodeprotonation of Bis(benzene)chromium by Using Mixed Alkali Metal-Magnesium Amide Bases and Structural Characterization of the Heterotrimetallic Products", *Angew. Chem. Int.* 44 (2005), pp. 68-72.

Hilf, et al. "The Equilibrium Between 2-Lithium-Oxazole(-Thiazole,-imidazole) Derivatives and Their Acyclic Isomers—A Structural Investigation", *Chem. Ber.I Recueil* 130 (1997), pp. 1213-1217.

Hodgson, et al. "Dimerization of Lithiated Terminal Aziridines", *Angew. Chem. Int.* 45 (2006), pp. 935-938.

Kauch, et al. "Synthesis of Halogenated Phenols by Directed *ortho*-Lithiation and *ipso*-Iododesilylation Reactions of O-Aryl N-Isopropylcarbamates", *Synthesis* 10 (2006), pp. 1578-1589.

Kim, et al. "Double Cycloisomerization asa Novel and Expeditious Route to Tricyclic Heteroaromatic Compounds: Short and Highly Diastereoselective Synthesis of (±)-Tetraponerine T6", *Organic Let.* 4 (2004), No. 26, pp. 4697-4699.

Kitagawa, et al. "Halogen-Magnesium Exchange cia Trialkylmagnesates for the Preparation of Aryl- and Alkenylmagnesium Reagents", *Angew. Chem. Int.* 39 (2000), No. 14, pp. 2481-2483.

Knaus, et al. "The Chemistry of Metalated Heterocycles, Dimerization of 2-Lithiomethyl-1,3-thiazoles,-1,3,4-thiadiazoles, and-1,3,4-oxadiazoles", *J. Org. Chem.* 39 (1974), No. 9, pp. 1189-1192.

Kneisel, et al. "Nucleophilic Catalysis of the Iodine—Zinc Exchange Reaction: Preparation of Highly Functionalized Diaryl Zinc Compounds", *Angew. Chem. Int.* 43 (2004), pp. 1017-1021.

Knochel, et al. "Synthesis and Reactivity toward Acyl Chlorydes and Enones of the New Highly Functionalized Copper Reagents RCu(CN)ZnI", *J. Org. Chem.* 53 (1988), pp. 2390-2392.

Kondo, et al. "Magnesiation of indoles with magnesium amide bases", *J, Chem. Soc.* 1 (1996), pp. 2331-2332.

Krasovskiy, et al. "Mixed Mg/Li Amides of the Type $R_2NMgClLiCl$ as Highly Efficient Bases for the Regioselective Generation of Functionalized Aryl and Heteroaryl Magnesium Compounds", *Angew. Chem. Int.* 45 (2006), pp. 2958-2961.

Leroux, et al. "α-Fluorinated Ethers, Thioethers, and Amines: Anomerically Biased Species", *Chem. Rev.* 105 (2005), pp. 827-856.

Lin, et al. "Highly Functionalized Benzene Syntheses by Directed Mono or Multiple Magnesiations with TMPMgClLiCl", *Organic Let.* 8 (2006), No. 24, pp. 5673-5676.

Meyers, et al. "Chemistry of Metalated Heterocycles, Rearrangement and Dimerization of Lithiothiazoles, Thiadiozoles, and Oxadiazoles", *J. Am. Chem. Soc.* 95:10 (1973), pp. 3408-3410.

Miller, et al. "A Convenient Oxazole C-2 Protecting Group: The Synthesis of 4- and 5-Substituted Oxazoles via Metalation of 2-Triisopropylsilyloxazoles", *J. Org. Chem.*, 70 (2005), pp. 9074-9076.

Mongin, et al. "Advances in the directed metallation of azines and diazines [ . . . ]", *Tetrahedron* 57 (2001). pp. 4059-4090.

Mosrin, et al. "Regio- and chemoselective magnesiation of protected uracils and thiouracils using TMPMgCl· LiCl and $TMP_2Mg$· 2LiCl", *Org. Biolol. Chem.* 6 (2008), pp. 3237-3239.

Mosrin, et al. "Regio- and Chemoselective Multiple Functionalization of Pyrimidine Derivatives by Selective Magnesiations using TMPMgCl· LiCl", *Org. Let.*, 10 (2008), No. 12, pp. 2497-2500.

Mosrin, et al. "Regio- and Chemoselective Metalation of Chloropyrimidine Derivatives with TMPMgCl· LiC and $TMP_2Zn$· $2MgCl_2$ 2LiCl", *Chem. Eur.* 15 (2009), pp. 1468-1477.

Mulvey, Robert E. "s-Block metal inverse crowns: synthetic and structural synergism in mixed alkali metal-magnesium (or zinc) amide chemistry", *Chem. Conn.* 2001, p. 1049.

Mulvey, Robert E. "Modern Ate Chemistry: Applications of Synergic Mixed Alkali-Metal-Magnesium or-Zinc Reagents in Synthesis and Structure Building", *Organometrics* 25 (2006), pp. 1060-1075.

Mulvey, et al. "Deprotonative Metalation Using Ate Compounds: Synergy, Synthesis, and Structure Building", *Angew. Chem. Int.* 46 (2007), pp. 3802-3824.

Naka, et al. "As Aluminum Ate Base: Its Design, Structure, Function, and Reaction Mechanism," *J. Am. Chem. Soc.* 129 (2007), pp. 1921-1930.

Negishi, Ei-ichi "Palladium- or Nickel-Catralyzed Cross Coupling. A New Selective Method for Carbon—Carbon Bond Formation", *Acc. Chem. Res.* 15 (1982), pp. 340-348.

Rabinov, et al. "Lithiation of Polychloropyrimidines and Dechloropyridines", *J. Org. Chem.*, 56 (1991), pp. 4793-4796.

Rohbogner, et al. "A General Method for *meta* and *para* Functionalization of Arenes Using $TMP_2Mg$ 2LiCl", *Angew. Chem. Int.* 47 (2008), pp. 1503-1507.

Sapountzis, et al. "General Preparation of Functionalized o-Nitroarylmagnesium Halides through an Iodine—Magnesium Exchange", *Angew. Chem. Int.* 41 (2002), No. 9, pp. 1610-1611.

Shilai, et al. "Selective metallation of thiophene and thiazole rings with magnesium amide base", *J. Chem. Soc., Perkin Trans.* No. 1 (2001), p. 442.

Sonogashira, et al. "A convenient synthesis of acelylenes: catalytic substitutions of acetylenic hydrogen with promoalkenes, iodoaremes, and bromoryridines", *Tetrahedron Let.* 50 (1975), pp. 4467-4470.

Tobrman, et al. "Selective Magnesiation of Chloro-iofopurines: An Efficient Approach to New Purine Derivatives", *Organic Let.* 8 (2006), No. 7, pp. 1291-1294.

Turck, et al. "Metalation of diazines. IV. Lithiation of *sym*-disubstituted pyrazines", *J. Organometr. Chem.* 412 (1991), pp. 301-310.

Turck, et al. "Advances in the directed metallation of azines and diazines [ . . . ]." *Tetrahedron* 57 (2001), pp. 4489-4505.

Uchiyama, et al. "Structure and Reaction Pathway of TMP-Zincate: Amido Base or Alkyl Base?", *J. Am/ Chem. Soc.* 128 (2006), pp. 8748-8750.

Villieras, et al. "Ethyl α-(Hydroxymethyl)Acrylate", *Org. Synth.* 8 (1993) p. 265.

Westerhausen, Matthias "Recent developments in the field of organic heterobimetallic compounds of the alkaline-earth metals", *Dalton Trans.* 2006, pp. 4755-4768.

Wunderlich, et al. "$(tmp)_2Zn$· $2MgCl_2$ 2LiCl: A Chemoselective Base for the Directed Zincation of Sensitive Arenes and Heteroarenes", *Angew. Chem. Int.* 46 (2007), pp. 7685-7688.

Wunderlich, et al. "Efficient *mono*- and *bis*-functionalization of 3,6-dechloropyridazine using $(tmp)_2Zn$· $2MgCl_2$ 2LiCl", *Chem. Commun.*, 2008, pp. 6387-6389.

Zang, et al. "BuMgN$i$Pr$_2$: A New Base for Stoichiometric, Position-Selective Deprotonation of Cyclopropane Carboxamides and Other Weak CH Acids", *Angew. Chem. Int.* 41 (2002), No. 12, pp. 2169-2171.

* cited by examiner

PRODUCTION AND USE OF ZINC AMIDES

RELATED APPLICATIONS

This application is a §371 application of PCT/EP2010/051677 filed Feb. 11, 2010, and claims priority from European Patent Application No, 09100112.3 filed Feb. 13, 2009.

Directed metalation of aromatic and heterocyclic compounds is an important method for the functionalization of these scaffolds. Lithium bases have been extensively used for performing the ortho-metalation of various unsaturated systems ((a) Snieckus, V. *Chem. Rev.* 1990, 90, 879. (b) Clayden, J.; Stimson, C. C.; Keenan M. *Chem. Comm.* 2006, 1393. (c) Schlosser M. *Angew. Chem. Int. Ed.* 2005, 44, 376. (d) Henderson, K. W.; Kerr, W. J. *Chem. Eur. J.* 2001, 3431. (e) Turck, A.; Plé, N.; Mongin, F.; Quéguiner, G. Tetrahedron 2001, 57, 4489. (f) Mongin F.; Quéguiner, G. *Tetrahedron* 2001, 57, 4059. (g) Levoux, F.; Jeschke, P.; Schlosser, M. *Chem. Rev.* 2005, 105, 827. (h) Kauch, M.; Hoppe, D. *Synthesis* 2006, 1578. (i) Clegg, W.; Dale, S. H.; Hevia, E.; Honeyman, G. W.; Mulvey R. E. *Angew. Chem. Int. Ed.* 2006, 45, 2371. (j) Hodgson, D. M.; Miles, S. M. *Angew. Chem. Int. Ed.* 2006, 45, 93. (k) Yus, M.; Foubelo, F. *Handbook of Functionalized Organometallics*, Knochel, P. Ed., Wiley-VCH: Weinheim, Germany 2005; Vol. 1, page 7). The use of magnesium bases, pioneered by Eaton, ((a) Eaton, P. E.; Martin, R. M. *J. Org. Chem.* 1988, 53, 2728. (b) Eaton, P. E.; Lee, C.-H.; Xiong, Y. *J. Am. Chem. Soc.* 1989, 111, 8016. (c) Eaton, P. E.; Lukin, K. A. *J. Am. Chem. Soc.* 1993, 115, 11370. (d) Zhang, M.-X.; Eaton, P. E. *Angew. Chem. Int. Ed.* 2002, 41, 2169) has recently found a renewed interest ((a) Hevia, E.; Honeyman, G. W.; Kennedy, A. R.; Mulvey, R. E.; Sherrington, D. C. *Angew. Chem. Int. Ed.* 2005, 44, 68. (b) Andrikopolous, P. C.; Armstrong, D. R.; Graham, D. V.; Hevia, E.; Kennedy, A. R.; Mulvey, R. E.; O'Hara, C. T.; Talmard, C. *Angew. Chem. Int. Ed.* 2005, 44, 3459. (c) Kondo, Y.; Akihiro, Y.; Sakamoto, T. *J. Chem. Soc., Perkin Trans.* 1 1996, 2331. (d) Shilai, M.; Kondo, Y.; Sakamoto, T. *J. Chem. Soc., Perkin Trans.* 1 2001, 442. (e) Bayh, O.; Awad, H.; Mongin, F.; Hoarau, C.; Bischoff, L.; Trécourt, F.; Quéguiner, G.; Marsais, F.; Blanco, F.; Abarca, B.; Ballesteros, R. *J. Org. Chem.* 2005, 70, 5190. (f) Eaton, P. E.; Zhang, M.-X.; Komiya, N.; Yang, C.-G.; Steele, I.; Gilardi, R. *Synlett* 2003, 9, 1275). Recently, lithium magnesiates ((a) Kitagawa, K.; Inoue, A.; Shinokubo, H.; Oshima, K. *Angew. Chem. Int. Ed.* 2000, 39, 2481. (b) Farkas, J.; Stoudt, S. J.; Hannawalt, E. M.; Pajeski, A. D.; Richey, H. G. *Organometallics* 2004, 23, 423. (c) Awad, H.; Mongin, F.; Trécourt, F.; Quéguiner, G.; Marsais, F.; Blanco, F.; Abarca, B.; Ballesteros, R. *Tetrahedron Lett.* 2004, 45, 6697; (a) Garcia-Alvarez, P.; Graham, D. V.; Hevia, E.; Kennedy, A. R.; Klett, J.; Mulvey, R. E.; O'Hara, C. T.; Weatherstone, S. *Angew. Chem. Int. Ed.* 2008, 47, 8079. (b) Mulvey, R. E. *Organometallics* 2006, 25, 1060. (c) Mulvey, R. E. *Chem. Comm.* 2001, 1049. (d) Westerhausen, M. *Dalton Trans.* 2006, 4755. (e) Mulvey, R. E.; Mongin, F.; Uchiyama, M.; Kondo, Y. *Angew. Chem. Int. Ed.,* 2007, 46, 3802) have found useful synthetic applications. Mixed Mg/Li-bases of type R$_2$NMgCl.LiCl such as 2,2,6,6-tetramethylpiperidide magnesium chloride—lithium chloride (TMPMgCl.LiCl; Turbo-Hauser base) proved to be especially effective metalating agent, compatible with functional groups such as an ester, a nitrile or an aryl ketone ((a) Krasovskiy, A.; Krasovskaya, V.; Knochel, P. *Angew. Chem. Int. Ed.* 2006, 45, 2958. (b) Lin, W.; Baron, O.; Knochel, P. *Org. Lett.* 2006, 8, 5673. (c) Mosrin, M.; Knochel, P. *Org. Lett.* 2008, 10, 2497. (d) Mosrin, M.; Boudet, N.; Knochel, P. *Org. BiomoL Chem.* 2008, 6, 3237. (e) Clososki, G. C.; Rohbogner, C. J.; Knochel, P. *Angew. Chem. Int. Ed.* 2007, 46, 7681. (f) Rohbogner, C. J.; Clososki, G. C.; Knochel, P. *Angew. Chem. Int. Ed.* 2008, 47, 1503). However, more sensitive functionalities such as an aldehyde or a nitro group are not tolerated. Also sensitive heterocycles may undergo fragmentation ((a) Micetich, R. G. *Can. J. Chem.* 1970, 48, 2006. (b) Meyers, A. I.; Knaus, G. N. *J. Am. Chem. Soc.* 1974, 95, 3408. (c) Knaus, G. N.; Meyers, A. I. *J. Org. Chem.* 1974, 39, 1189. (d) Miller, R. A.; Smith, M. R.; . Marcune, B. *J. Org. Chem.* 2005, 70, 9074. (e) Hilf, C.; Bosold, F.; Harms, K.; Marsch, M.; Boche, G. *Chem. Ber. Rec.* 1997, 130, 1213). Therefore a range of zinc amides have been reported which provide after metalation organozinc reagents compatible with most functionalities. In pioneer work, lithium di-tert-butyl-(2,2,6,6-tetra-methylpiperidino) zincate (Lit-Bu$_2$TMPZn) was reported by Kondo to be an excellent base for the zincation of various aromatics ((a) Micetich, R. G. *Can. J. Chem.* 1970, 48, 2006. (b) Meyers, A. I.; Knaus, G. N. *J. Am. Chem. Soc.* 1974, 95, 3408. (c) Knaus, G. N.; Meyers, A. I. *J. Org. Chem.* 1974, 39, 1189. (d) Miller, R. A.; Smith, M. R.; Marcune, B. *J. Org. Chem.* 2005, 70, 9074. (e) Hilf, C.; Bosold, F.; Harms, K.; Marsch, M.; Boche, G. *Chem. Ber. Rec.* 1997, 130, 1213). Unfortunately, the use of highly reactive zincates or related ate-bases ((a) Uchiyama, M.; Matsumoto, Y.; Nobuto, D.; Furuyama, T.; Yamaguchi, K.; Morokuma, K. *J. Am. Chem. Soc.* 2006, 128, 8748. (b) Clegg, W.; Dale, S. H.; Drummond, A. M.; Hevia, E.; Honeyman, G. W.; Mulvey, R. E. *J. Am. Chem. Soc.* 2006, 128, 7434. (c) Hevia, E.; Honeyman, G. W.; Mulvey, R. E. *J. Am. Chem. Soc.* 2005, 127, 13106. (d) Armstrong, D. R.; Clegg, W.; Dale, S. H.; Hevia, E.; Hogg, L. M.; Honeyman, G. W.; Mulvey, R. E. *Angew. Chem. Int. Ed.* 2006, 45, 3775. (e) Clegg, W.; Dale, S. H.; Harrington, R. W.; Hevia, E.; Honeyman, G. W.; Mulvey, R. E. *Angew. Chem. Int. Ed.* 2006, 45, 2374. (f) Naka, H.; Uchiyama, M.; Matsumoto, Y.; Wheatly, A. E. H.; McPartlin, M.; Morey, J. V.; Kondo, Y. *J. Am. Chem. Soc.* 2007, 129, 1921) is not compatible with sensitive functions such as an aldehyde or a nitro group. Recently, we have reported the preparation of a highly chemoselective base TMP$_2$Zn.2MgCl$_2$.2LiCl for the directed zincation of sensitive aromatics and heteroaromatics ((a) Wunderlich, S. H.; Knochel, P. *Angew. Chem. Int. Ed.* 2007, 46, 7685. (b) Mosrin, M.; Knochel P. *Chem. Eur. J.* 2009, DOI: 10.1002/chem.200801831). However, some electron-poor functionalized arenes and heteroarenes still give with this reagent, unsatisfactory results in terms of yields and reaction selectivity. Moreover, several activated aromatics or heteroaromatics like nitro derivatives or pyridazines require metalations below −50° C., which is not convenient for the reaction upscaling ((a) Wunderlich, S. H.; Knochel, P. *Angew. Chem. Int. Ed.* 2007, 46, 7685. (b) Mosrin, M.; Knochel P. *Chem. Eur. J.* 2009, DOI: 10.1002/chem.200801831; Wunderlich, S. H.; Knochel, P. *Chem. Comm.* 2008, 47, 6387).

A reagent of the general formula

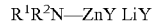

(I)

wherein

R$^1$, R$^2$ are, independently, selected from H, substituted or unsubstituted aryl or heteroaryl containing one or more heteroatoms, linear, branched or cyclic, substituted or unsubstituted alkyl, alkenyl, alkynyl, or silyl derivatives thereof; and R$^1$ and R$^2$ together can be part of a cyclic or polymeric structure; and wherein at least one of R$^1$ and R$^2$ is other than H; Y is selected from the group consisting of F; Cl; Br; I; CN; SCN; NCO; HalO$_n$, wherein n=3 or 4 and Hal is selected from Cl, Br and I; NO$_3$; BF$_4$; PF$_6$; H; a carboxylate of the general formula R$^5$CO$_2$ ; an alcoholate of the general formula OR$^5$; a thiolate of the general formula $SR^5$; $R^5P(O)O_2$; or $SCOR^5$; or $SCSR^5$; $O_nSR^5$, wherein n=2 or 3; or $NO_n$, wherein n=2 or 3; and a derivative thereof; wherein $R^5$ is a substituted or unsubstituted aryl or heteroaryl containing one or more heteroatoms, linear, branched or cyclic, substituted or unsubstituted alkyl; alkenyl, alkynyl, or derivatives thereof, or H;
or as adduct with a solvent.

$R^1$, $R^2$ are cyclic and substituted by $R^3$, and $R^4$ that are, independently, selected from H, substituted or unsubstituted aryl or heteroaryl containing one or more heteroatoms. linear, branched or cyclic, substituted or unsubstituted alkyl, alkenyl, alkynyl, or silyl derivatives thereof; and $R^1$ and $R^2$ together, or $R^3$ and $R^4$ together can be part of a cyclic or polymeric structure; and wherein at least one of $R^1$ and $R^2$ and at least one of $R^3$ and $R^4$ is other than H.

Preferable the reagent $R^1R^2N$—ZnY LiY (I) is 2,2,6,6-Tetramethylpiperide Zinc Chloride Lithium Chloride or the solution of the reagent in a solvent. The solvent is polar and aprotic. Preferable is the solvent selected from cyclic, linear or branched mono or polyethers, thioethers, amines, phosphines, and derivatives thereof containing one or more additional heteroatoms selected from O, N, S and P, preferably tetrahydrofuran (THF), 2-methyltetrahydrofuran, dibutyl ether, diethyl ether, tert- butylmethyl ether, dimethoxyethane, dioxanes, preferably 1,4-dioxane, triethylamine, ethyldiisopropyl amine, dimethylsulfide, dibutylsulfide; cyclic amides, preferably N—methyl-2-pyrrolidone (NMP), N-ethyl-2-pyrrolidone (NEP), N-butyl-2-pyrrolidone (NBP); cyclic, linear or branched alkanes and/or alkenes wherein one or more hydrogens are replaced by a halogen, preferably dichloromethane, 1,2-dichloroethane, $CCl_4$; urea derivatives, preferably N,N'-dimethylpropyleneurea (DMPU); aromatic, heteroaromatic or aliphatic hydrocarbons, preferably benzene, toluene, xylene, pyridine, pentane, cyclohexane, hexane, heptane; hexamethylphosphorus triamide (HMPA), $CS_2$; or combinations thereof.

The inventive process for the preparation of a mixed Zn/Li amide comprises the reaction in a solvent a primary or secondary amine with a lithium alkyl.

Preferable comprises the process for the preparation of a reagent having the general formula

$$R^1R^2N\text{—}ZnY\ LiY \qquad (I)$$

wherein
$R^1$, $R^2$ are, independently, selected from H, substituted or unsubstituted aryl or heteroaryl containing one or more heteroatoms, linear, branched or cyclic, substituted or unsubstituted alkyl, alkenyl, alkynyl, or silicon derivatives thereof; and $R^1$ and $R^2$ together can be part of a cyclic or polymeric structure; and wherein at least one of $R^1$ and $R^2$ is other than H; Y is selected from the group consisting of F; Cl; Br; I; CN; SCN; NCO; $HalO_n$, wherein n=3 or 4 and Hal is selected from Cl, Br and I; $NO_3$; $BF_4$; $PF_6$; H; a carboxylate of the general formula $R^5CO_2$; an alcoholate of the general formula $OR^X$; a thiolate of the general formula $SR^5$; $R^5P(O)O_2$; or $SCOR^5$; or $SCSR^5$; $O_nSR^5$, wherein n=2 or 3; or $NO_n$, wherein n=2 or 3; and a derivative thereof;
wherein $R^5$ is a substituted or unsubstituted aryl or heteroaryl containing one or more heteroatoms, linear, branched or cyclic, substituted or unsubstituted alkyl, alkenyl, alkynyl, or derivatives thereof, or H;
and the reaction is carried out in a solvent of $R^1R^2N$—H with $R^5Li$ in the presence of $ZnY_2$ and X is defined as Y above.

X and Y are independently or both Cl, Br or I, and preferably Cl. The lithium organyl reagent is sec-butyl-Li and the solvent is selected from cyclic, linear or branched mono or polyethers, thioethers, amines, phosphines, and derivatives thereof containing one or more additional heteroatoms selected from O, N, S and P, preferably tetrahydrofuran (THF), 2-methyltetrahydrofuran, dibutyl ether, diethyl ether, tert-butylmethyi ether, dimethoxyethane, dioxanes, preferably 1,4-dioxane, triethylamine, ethyldiisopropylamine, dimethylsulfide, dibutylsulfide; cyclic amides, preferably N— methyl-2-pyrrolidone (NMP), N-ethyl-2-pyrrolidone (NEP), N-butyl-2-pyrrolidone (NBP); cyclic, linear or branched alkanes and/or alkenes wherein one or more hydrogens are replaced by a halogen, preferably dichloromethane, 1,2-dichloroethane, $CCl_4$; urea derivatives, preferably N,N'-dimethylpropyleneurea (DMPU); aromatic, hetero aromatic or aliphatic hydrocarbons, preferably benzene, toluene, xylene, pyridine, pentane, cyclohexane, hexane, heptane; hexamethyiphosphorus triamide (HMPA), $CS_2$; or combinations thereof.

Unless otherwise defined, all technical and scientific terms used herein have the same meaning as commonly understood by one of ordinary skill in the art to which this invention belongs. All publications and other references mentioned herein are incorporated by reference in their entirety.

As used herein, the terms "alkyl", "alkenyl" and "alkynyl" refer to linear, cyclic and branched, substituted and unsubstituted $C_1$-$C_{20}$ compounds. Preferred ranges for these compounds are $C_1$-$C_{10}$, preferably $C_1$-$C_5$ (lower alkyl) and $C_2$-$C_{10}$ and preferably $C_2$-$C_5$, respectively, for alkenyl and alkynyl. The term "cycloalkyl" generally refers to linear and branched, substituted and unsubstituted $C_3$-$C_{20}$ cycloalkanes. Here, preferred ranges are $C_3$-$C_{15}$, more preferably $C_3$-$C_8$.

Whenever any of the residues $R^1$, $R^2$, $R^3$ and/or $R^4$ are substituted by a substituent, the substituent may be selected by a person skilled in the art from any known substituent. A person skilled in the art will select a possible substituent according to his knowledge and will be able to select a substituent which will not interfere with other substituents present in the molecule and which will not interfere or disturb possible reactions, especially the reactions described within this application. Possible substituents include without limitation
halogens, preferably fluorine, chlorine, bromine and iodine;
aliphatic, alicyclic, aromatic or heteroaromatic hydrocarbons, especially alkanes, alkylenes, arylenes, alkylidenes, arylidenes, heteroarylenes and heteroarylidenes; carbonxylic acids including the salts thereof;
carboxylic acid halides;
aliphatic, alicyclic, aromatic or heteroaromatic carboxylilc acid esters;
aldehydes;
aliphatic, alicyclic, aromatic or heteroaromatic ketones;
alcohols and alcoholates, including a hydroxyl group;
phenoles and phenolates;
aliphatic, alicyclic, aromatic or heteroaromatic ethers;
aliphatic, alicyclic, aromatic or heteroaromatic peroxides;
hydroperoxides;
aliphatic, alicyclic, aromatic or heteroaromatic amides or amidines;
nitriles;
aliphatic, alicyclic, aromatic or heteroaromatic amines;
aliphatic, alicyclic, aromatic or heteroaromatic imines;
aliphatic, alicyclic, aromatic or heteroaromatic sulfides including a thiol group;
sulfonic acids including the saits thereof;
thioles and thiolates;
phosphonic acids ineluding the salts thereof;

phosphinic acids including the salts thereof;
phosphorous acids including the salts thereof; phosphinous acids including the salts thereof.

The substituents may be bound to the residues $R^1$, $R^2$, $R^3$ and/or $R^4$ via a carbon atom, an oxygen atom, a nitrogen atom, a sulfur atom, or a phosphorus atom. The hetero atoms in any structure containing hetero atoms, as e.g. heteroarylenes or heteroaromatics, may preferably be N, O, S and P.

When $R^1$ and $R^2$, or $R^3$ and $R^4$ can be part of a cyclic structure, it is to be understood that $R^1$ and $R^2$ together, or $R^3$ and $R^4$ together, are a divalent saturated or unsaturated, linear or branched alkyl, alkenyl or alkynyl which forms in connection with the nitrogen atom of the amide a cyclic secondary amide. An example of such a cyclic amide is the amide of TMPH. Further, the residues $R^1$ and $R^2$, and/or $R^3$ and $R^4$ can be part of a polymeric structure. The nitrogen atom of the amide is the connected to a polymeric backbone which may even contain more than one nitrogen atom for the formation of an amide according to the invention.

The term "aryl" as used herein refers to substituted or unsubstituted $C_4$-$C_{24}$ aryl. By "heteroaryl", a substituted or unsubstituted $C_3$-$C_{24}$ aryl, containing one or more heteroatoms as B, O, N, S, Se, P, is meant. Preferred ranges for both are $C_4$-$C_{15}$, more preferably $C_4$-$C_{10}$, and includes aryls and fused aryls with or without heteroatoms, A preferred ring size comprises 5 or 6 ring atoms.

For example, we have explored the preparation of more selective zinc base which would allow chemoselective metalations at 25° C. for the directed zincation of sensitive aryl and heteroaryl substrates. The treatment of 2,2,6,6-tetramethylpiperidine (1; TMP-H) with n-BuLi (1.0 equiv, −40 to −10° C., 1 h) followed by the addition of $ZnCl_2$ (1.1 equiv, −10° C., 30 min) provides a ca. 1.3 M solution of TMPZnCl.LiCl (2), stable at room temperature (Scheme 1). In constrast to $TMP_2Zn.2MgCl_2.2LiCl$, this complex base showed a very good chemoselectivity for the zincation at 25° C. of various sensitive aromatics and heterocycles.

Scheme 1: Preparation of 2,2,6,6-Tetramethylpiperidide Zinc Chloride Lithium Chloride (TMPZnCl•LiCl) (2)

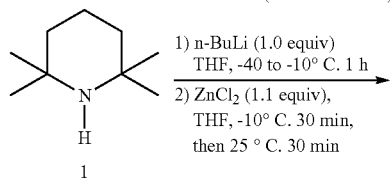

2: TMPZnCl•LiCl > 95%

The inventive reagent could be used in a reaction with an electrophile preferably for the deprotonation of any substrate which can form stabilized or unstabilized carbaniones.

Examples for the use of the reagent according to the invention are given in the following tables.

TABLE 1

Products Obtained by Regio- and Chemoselective Zincation of Diazines of Type 3, 6 and 9 with TMPZnCl•LiCl (2; 1.1 equiv; 25° C.) and Quenching with Electrophiles

| entry | substrate of type 3, 6 and 9 | electrophile | product | yield, %[a] |
|---|---|---|---|---|
| 1 | (3) 3,6-dichloropyridazine | $I_2$ | (5a) 3,6-dichloro-4-iodopyridazine | 84 |
| 2 | 3 | 4-fluorobenzoyl chloride | (5b) (3,6-dichloropyridazin-4-yl)(4-fluorophenyl)methanone | 96[b] |

TABLE 1-continued

Products Obtained by Regio- and Chemoselective Zincation of Diazines of Type 3, 6 and 9 with TMPZnCl·LiCl (2; 1.1 equiv; 25° C.) and Quenching with Electrophiles

| entry | substrate of type 3, 6 and 9 | electrophile | product | yield, %[a] |
|---|---|---|---|---|
| 3 | 3 | 3-iodobenzotrifluoride (I-C6H4-CF3) | 5c | 83[c] |
| 4 | 6 | I2 | 8a | 83 |
| 5 | 6 | furoyl chloride | 8b | 71[b] |
| 6 | 6 | allyl bromide | 8c | 89[d] |
| 7 | 9 | I2 | 11a | 90 |
| 8 | 9 | ethyl 4-iodobenzoate | 11b | 87[c] |

TABLE 1-continued

Products Obtained by Regio- and Chemoselective Zincation of Diazines of Type 3, 6 and 9 with TMPZnCl•LiCl (2; 1.1 equiv; 25° C.) and Quenching with Electrophiles

| entry | substrate of type 3, 6 and 9 | electrophile | product | yield, %[a] |
|---|---|---|---|---|
| 9 | 9 | ![Br-CH2-C(=CH2)-CO2Et] | 11c | 72[d] |

[a]Isolated, analytically pure product;
[b]Transmetalation performed with 1.1 equiv of CuCN•2 LiCl;
[c]Obtained by palladium-catalyzed cross-coupling using Pd(dba)₂ (3 mol %) and (o-furyl)₃P (6 mol %);
[d]Transmetalation performed with 5 mol % of CuCN• 2 LiCl.

Scheme 2: Zincation of 3,6-Dichloropyridazine (3), 4,6-Dichloropyrimidine (6) and 2,6-Dichloropyrazine (9) using TMPZnCl•LiCl (2; 1.1 equiv; 25° C.) and Trapping with Electrophiles

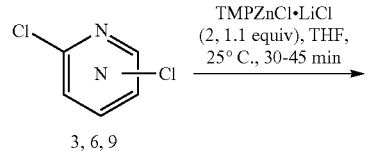

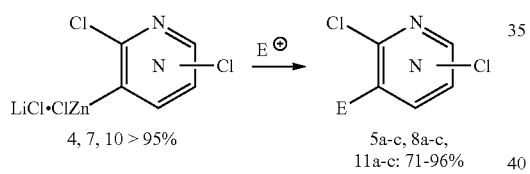

Several sensitive heteroarenes such as pyridazines, (Wunderlich, S. H.; Knochel, P. *Chem. Comm.* 2008, 47, 6387) pyrimidines ((a) Turck, A.; Plé, N.; Quéguiner, G. *Heterocycles* 1990, 37, 2149. (b) Radinov, R.; Chaney, C.; Haimova, M. *J. Org. Chem.* 1991, 56, 4793 and pyrazines (Turck A.; Trohay, D.; Mojovic, L.; Plé, N.; Quéguiner, G. *J. Organomet. Chem.* 1991, 412, 301)) are cleanly zincated at 25° C. using the new base TMPZnCl.LiCl(2; Scheme 2 and Table 1). Thus, the treatment of 3,6-dichloropyridazine (3) with TMPZnCl.LiCl (2; 1.1 equiv, 25° C., 30 min) leads to the zincated species (4), which can be trapped with I₂, 4-fluorobenzoyl chloride (after transmetalation with CuCN.2LiCl) (Knochel, P.; Yeh, M. C. P.; Berk, S. C.; Talbert, J. *J. Org. Chem.* 1988, 53, 2390) or undergo a Negishi (Negishi, E.; *Acc. Chem. Res.* 1982, 15, 340) cross-coupling leading to the expected products 5a-c in 83-96% yields (entries 1-3 of Table 1). Zincations of other sensitive heteroaromatics can be readily achieved by the addition of TMPZnCl.LiCl (2). Thus, 4,6-dichloropyrimidine (6) is converted within 45 min at 25° C. to the 5-zincated species. Trapping with I₂ is furnishing the iodopyrimidine 8a in 83% yield (entry 4). Reaction with furoyl chloride (after transmetalation with CuCN.2LiCl) (Knochel, P.; Yeh, M. C. P.; Berk, S. C.; Talbert, J. *J. Org.*  *Chem.* 1988, 53, 2390) provides the 5-ketopyrimidine 8b in 71% (entry 5). An allylation (after addition of CuCN.2LiCl) leads to the allyled derivative 8c in 89% (entry 6). Similarly, 2,6-dichloropyrazine (9) is zincated quantitatively with TMPZnCl.LiCl(2; 1.1 equiv, 25° C., 30 min) and reacted with iodine or undergoes a Negishi (Negishi, E.; *Acc. Chem. Res.* 1982, 15, 340) cross-coupling or an allylation with ethyl 2-(bromomethyl)acrylate (Villiéres, J.; Rambaud, M. *Org. Synth.* 1988, 66, 220) (after addition of CuCN.2LiCl) affording the expected products 11a-c in 72-90% yields (entries 7-9).

Scheme 3: Zincation of Caffeine (12) using TMPZnCl•LiCl (2; 1.1 equiv; 25° C.) and Trapping with Electrophiles

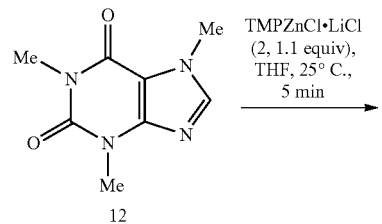

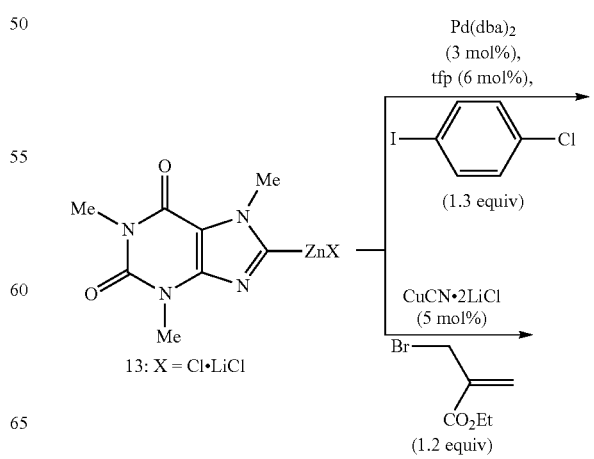

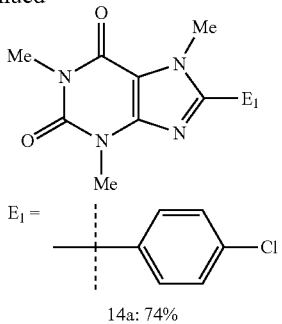

14a: 74%

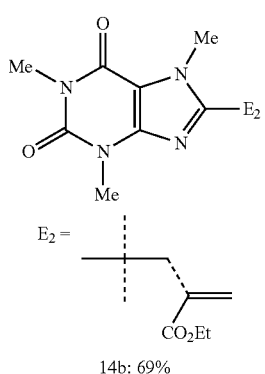

14b: 69%

Other sensitive heterocycles such as purines ((a) Boudet, N; Dubbaka, S. R.; Knochel, P. *Org. Lett* 2007, 10, 1715. (b) Tobrman, T.; Dvorák, D. *Org. Lett.* 2006, 8, 1291) can be metalated as well under mild conditions (Scheme 3). Thus, caffeine (12) (Do, H-Q; Kashif-Khan R. M.; Daugulis, O. *J. Am. Chem. Soc.* 2008, 130, 15185) undergoes a smooth zincation using TMPZnCl.LiCl (2; 1.1 equiv, 25° C., 5 min) furnishing the zinc species 13. Negishi (Negishi, E.; *Acc. Chem. Res.* 1982, 15, 340) cross-coupling or trapping with ethyl 2-(bromomethyl)acrylate (Villiéras, J.; Rambaud, M. *Org. Synth.* 1988, 66, 220) (after addition of CuCN.2LiCl) lead to the purine derivative 14a and 14b in 74 and 69% yields respectively.

A unique advantage of the zinc base 2 is that very sensitive functional groups such as a nitro group can be tolerated at 25° C. (I. Sapountzis, P. Knochel, *Angew. Chem. Int. Ed.* 2002, 41, 1610). Thus, 2,4-difluoronitrobenzene (15) was converted to the corresponding zinc reagent 16 by treatment with TMPZn-Cl.LiCl (2; 1.1 equiv, 25° C., 45 min). A Negishi (Negishi, E.; *Acc. Chem. Res.* 1982, 15, 340) cross-coupling can be readily performed to furnish the aryl derivative 17a in 92% yield (Scheme 4). Trapping with benzoyl chloride (after transmetalation with CuCN.2LiCl) (Knochel, P.; Yeh, M. C. P.; Berk, S. C.; Talbert, J. *J. Org. Chem.* 1988, 53, 2390) provides the ketone 17b in 84% yield. After trapping with I$_2$, the iodobenzene derivative 17c was obtained in 90% yield.

Scheme 4. Zincation of 2,4-Difluoronitrobenzene (15) using TMPZnCl•LiCl (2; 1.1 equiv; 25° C.) and Trapping with Electrophiles

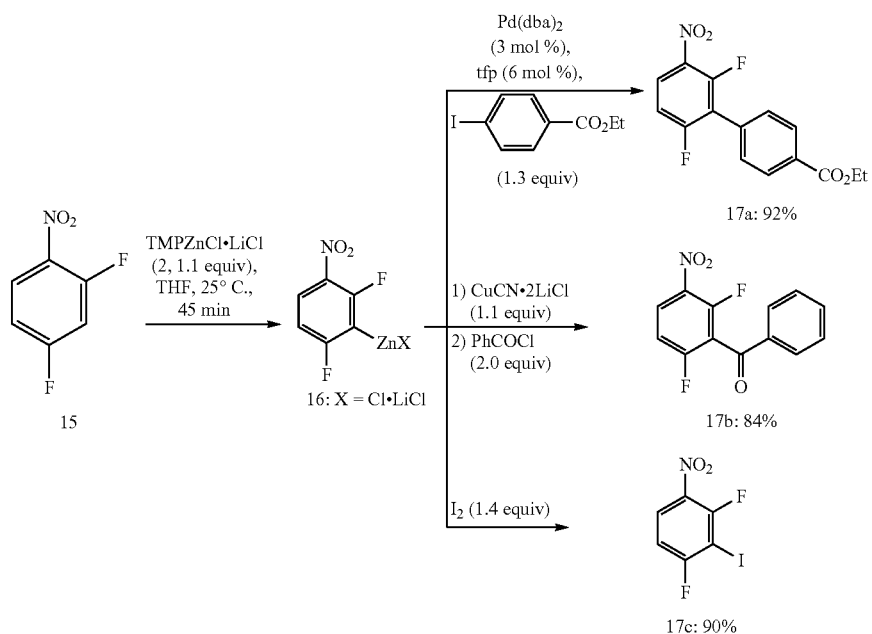

Other sensitive electron-poor arenes and heteroarenes are metalated as well using 2. Thus, 2-chloro-3-nitropyridine (18) undergoes smooth metalation with TMPZnCl.LiCl (2; 1.1 equiv, 25° C., 45 min) furnishing the zinc species 19. Trapping using 3-bromocyclohexene (after addition of CuCN.2LiCl) provides the pyridine 20 in 73% yield. Similarly, 4-fluoro-1-methoxy-2-nitrobenzene (21) was converted within 6 h at 25° C. to the corresponding zinc reagent 22. Quenching with ethyl 2-(bromomethyl)acrylate (Villiéras, J.; Rambaud, M. *Org. Synth.* 1988, 66, 220) (after addition of CuCN.2LiCl) leads to the allyled derivative 23 in 67% yield. Zincation of methyl 5-nitrofuran-2-carboxylate (24) can also be readily carried out using 2 (1.1 equiv) and furnishes the zinc species 25 in 30 min at 25° C. Allylation with 3-bromocyclohexene (after addition of CuCN.2LiCl) gives the furan 26 in 72% yield.

Scheme 5: Zincation of 2-Chloro-3-nitropyridine (18), 4-Fluoro-1-methoxy-2-nitrobenzene (21) and Methyl 5-nitrofuran-2-carboxylate (24) using TMPZnCl•LiCl (2; 1.1 equiv, 25° C.) and Trapping with Electrophiles

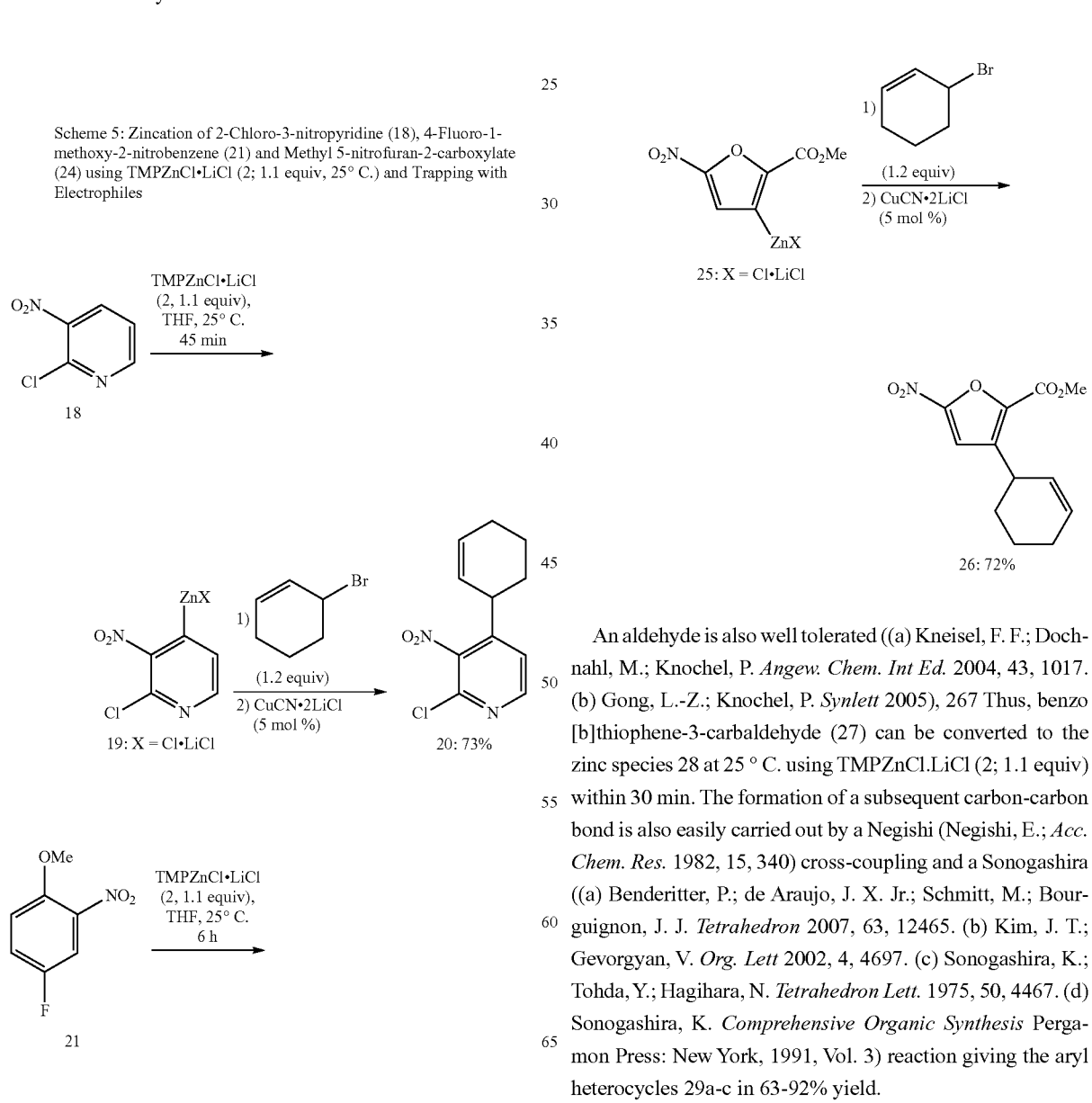

An aldehyde is also well tolerated ((a) Kneisel, F. F.; Dochnahl, M.; Knochel, P. *Angew. Chem. Int Ed.* 2004, 43, 1017. (b) Gong, L.-Z.; Knochel, P. *Synlett* 2005), 267 Thus, benzo[b]thiophene-3-carbaldehyde (27) can be converted to the zinc species 28 at 25 ° C. using TMPZnCl.LiCl (2; 1.1 equiv) within 30 min. The formation of a subsequent carbon-carbon bond is also easily carried out by a Negishi (Negishi, E.; *Acc. Chem. Res.* 1982, 15, 340) cross-coupling and a Sonogashira ((a) Benderitter, P.; de Araujo, J. X. Jr.; Schmitt, M.; Bourguignon, J. J. *Tetrahedron* 2007, 63, 12465. (b) Kim, J. T.; Gevorgyan, V. *Org. Lett* 2002, 4, 4697. (c) Sonogashira, K.; Tohda, Y.; Hagihara, N. *Tetrahedron Lett.* 1975, 50, 4467. (d) Sonogashira, K. *Comprehensive Organic Synthesis* Pergamon Press: New York, 1991, Vol. 3) reaction giving the aryl heterocycles 29a-c in 63-92% yield.

Scheme 6: Zincation of Benzo[b]thiophene-3-carbaldehyde (27) using TMPZnCl•LiCl (2; 1.1 equiv; 25° C.) and Trapping with Electrophiles

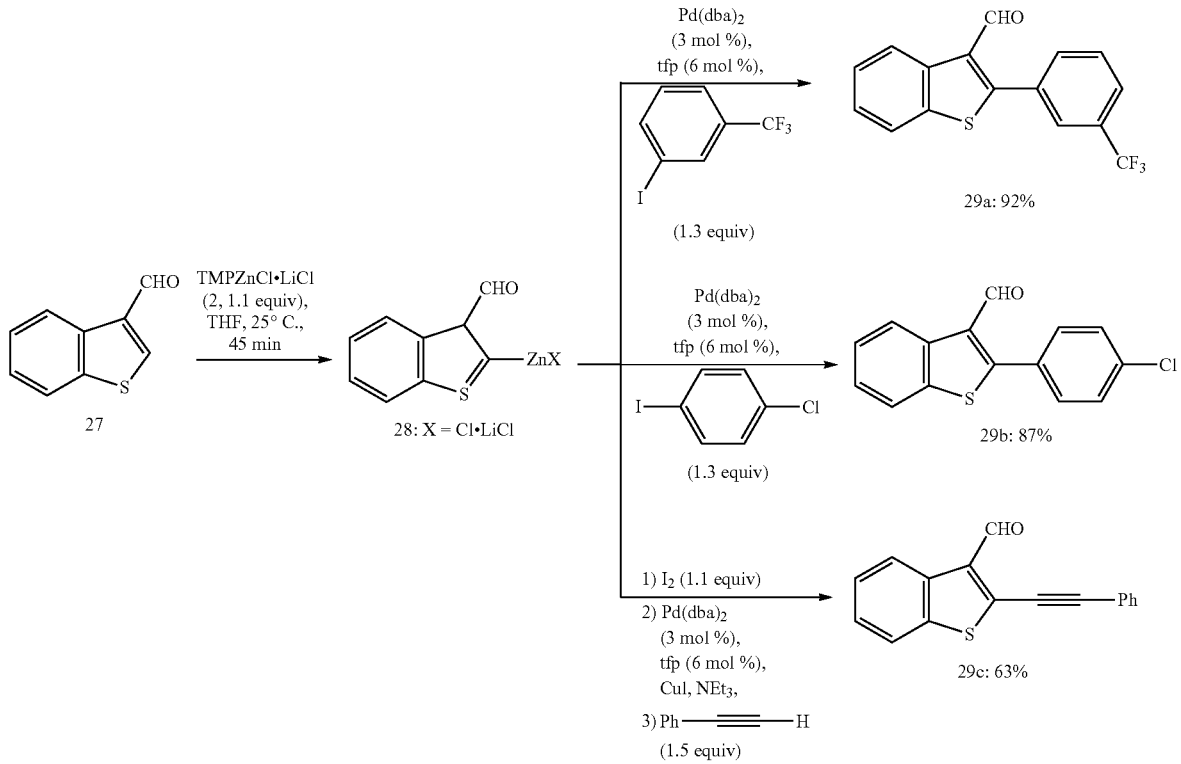

2) EXPERIMENTAL PROCEDURES AND ANALYTICAL DATA

Typical Procedure 1: Preparation of the reagent TMPZnCl.LiCl (2):

A dry and argon flushed 250 mL Schlenk-flask, equipped with a magnetic stirrer and a septum, was charged with freshly 2,2,6,6-tetramethylpiperidine (10.22 mL, 60 mmol) dissolved in THF (60 mL). This solution was cooled to −40° C. and n-BuLi (2.4 M in hexane, 25 mL, 60 mmol) was dropwise added. After the addition was complete, the reaction mixture was allowed to warm up slowly to −10° C. for 1 h. ZnCl$_2$ (1.0 M in THF, 66 mL, 66 mmol) was dropwise added and the resulting solution was stirred for 30 min at −10° C. and then for 30 min at 25° C. The solvents were then removed under vacuum affording a yellowish solid. Freshly distilled THF was then slowly added under vigorous stirring until the salts were completely dissolved. The freshly prepared TMPZnCl.LiCl (2) solution was titrated prior to use at 25° C. with benzoic acid using 4-(phenyiazo)diphenylamine as indicator. A concentration of 1.3 M in THF was obtained.

Typical Procedure for the Zincation of Polyfunctionalized Aromatics and Heterocycles with TNIPZnCl.-LiCl (TP 2):

A dry and argon flushed 10 mL Schlenk-flask, equipped with a magnetic stirring bar and a septum was charged with the zinc base (2; 1.1 equiv). After setting the desired temperature (Table 1), a solution of the corresponding arene (1.0 mmol) in dry THF (2 mL) was dropwise added and stirred at the same temperature. The completion of the metalation was checked by GC-analysis of reaction aliquots quenched with a solution of I$_2$ in dry THF.

Synthesis of 3,6-dichloro-4-iodopyridazine (5a)

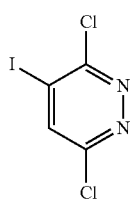

3,6-Dichloropyridazine (3) (149 mg, 1.0 mmol) in THF (2 mL) was added to a solution of TMPZnCl.LiCl (2) (1.3 M in THF, 0.85 mL, 1.1 mmol) at 25° C. and the reaction mixture was then stirred at this temperature for 30 min according to TP 2. I$_2$ (381 mg, 1.5 mmol) dissolved in dry THF (2 mL) was then dropwise added and the resulting mixture was stirred for 0.5 h. The reaction mixture was quenched with a sat. aq. Na$_2$S$_2$O$_3$ solution (10 mL) and with a sat. aq. NH$_4$Cl solution (20 mL), extracted with diethyl ether (3×50 mL) and dried over anhydrous Na$_2$SO$_4$. After filtration, the solvent was evaporated in vacuo. Purification by flash-chromatography (CH$_2$Cl$_2$/n-pentane, 1:2) furnished compound 5a (231 mg, 84%) as a colourless solid.

m.p.: 145.1-146.6° C.

$^1$H-NMR (300 MHz, CDCl$_3$) δ: 8.06 (s, 1 H).

$^{13}$C-NMR (75 MHz, CDCl$_3$) δ: 159.7, 153.9, 139.7, 105.4.

MS (70 eV, EI) m/z (%): 274 (95) [M$^+$], 127 (23), 123 (10), 121 (10), 119 (100), 86 (15), 84 (43), 49 (8).

IR (ATR) ṽ (cm$^{-1}$): 3092, 3020, 1796, 1516, 1488, 1464, 1332, 1296, 1276, 1236, 1152, 1136, 1060, 1044, 992, 956, 900, 812, 764, 728, 672, 660, 628, 608, 588, 564.

HRMS (EI) for C$_4$HCl$_2$IN$_2$ (273.8561): 273.8538.

Synthesis of (3,6-dichloropyridazin-4-yl)(4-fluorophenyl)methanone (5b)

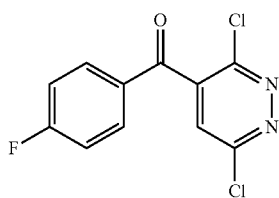 [SMILES: O=C(c1ccc(F)cc1)c1cc(Cl)nnc1Cl]

3,6-Dichloropyridazine (3) (149 mg, 1.0 mmol) in THF (2 mL) was added to a solution of TMPZnCl.LiCl (2) (1.3 M in THF, 0.85 mL, 1.1 mmol) at 25° C. and the reaction mixture was then stirred at this temperature for 30 min according to TP 2. After cooling down to −20° C., CuCN.2LiCl (1.0 M in THF, 1.1 mmol, 1.1 equiv) was added and the resulting mixture was stirred for 30 min at this temperature. 4-Fluorobenzoyl chloride (317 mg, 2.0 mmol) was then slowly added and the resulting mixture was allowed to warm up slowly to 10° C. The reaction mixture was quenched with a sat. aq. NH$_4$Cl solution (20 mL), extracted with diethyl ether (3×50 mL) and dried over anhydrous Na$_2$SO$_4$. After filtration, the solvent was evaporated in vacuo. Purification by flash-chromatography (CH$_2$Cl$_2$/n-pentane, 1:1) furnished compound 5b (259 mg, 96%) as a white solid.

m.p.: 71.1-72.6° C.

$^1$H-NMR (400 MHz, CDCl$_3$) δ: 7.79-7.83 (m, 2 H), 7.51 (s, 1 H), 7.19-7.24 (m, 2 H).

$^{13}$C-NMR (100 MHz, CDCl$_3$) δ: 187.4, 167.0 (d, J (C-F)=259.9 Hz), 156.3, 151.5, 139.6, 132.8 (d, J(C-F)=9.9 Hz), 130.4 (d, J(C-F)=3.1 Hz), 127.7, 116.8 (d, J(C-F)=22.6 Hz).

MS (70 eV, EI) m/z (%): 270 (11) [M$^+$], 123 (100), 95 (19).

IR (ATR) ṽ (cm$^{-1}$): 3067, 2927, 2358, 1917, 1673, 1590, 1504, 1414, 1344, 1319, 1256, 1237, 1178, 1157, 1140, 1103, 1041, 1009, 967, 955, 909, 849, 841, 818, 795, 760, 753, 683, 659, 650, 645, 638, 633, 625, 620, 614, 606, 602.

HRMS (EI) for C$_{11}$H$_5$Cl$_2$FN$_2$O (269.9763): 269.9762.

Synthesis of 3,6-dichloro-4-(3-(trifluoromethyl)phenyl)pyridazine (5c)

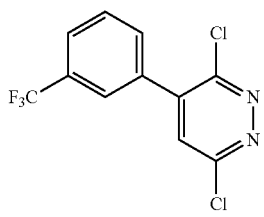

3,6-Dichloropyridazine (3) (149 mg, 1.0 mmol) in THF (2 mL) was added to a solution of TMPZnCl.LiCl (2) (1.3 M in THF, 0.85 mL, 1.1 mmol) at 25 ° C. and the reaction mixture was then stirred at this temperature for 30 min according to TP 2. Pd(dba)$_2$ (17 mg, 3 mol %) and P(o-furyl)$_3$ (14 mg, 6 mol %) dissolved in THF (2 mL), and mixed with 3-iodobenzomethyltrifluoride (354 mg, 1.3 mmol, 1.3 equiv) were then transferred via cannula to the reaction mixture. The resulting mixture was stirred for 1 h at 25° C. The reaction mixture was then quenched with a sat. aq. NH$_4$Cl solution (20 mL), extracted with diethyl ether (3×50 mL) and dried over anhydrous Na$_2$SO$_4$. After filtration, the solvent was evaporated in vacuo. Purification by flash-chromatography (CH$_2$Cl$_2$/n-pentane, 1:2) furnished compound 5c (243 mg, 83%) as a colourless solid.

m.p.: 93.0-94.9 ° C.

$^1$H-NMR (400 MHz, CDCl$_3$) δ: 7.66-7.81 (m, 4 H), 7.53 (s, 1 H).

$^{13}$C-NMR (100 MHz, CDCl$_3$) δ: 156.1, 154.4, 143.3, 141.2, 133.9, 131.5 (q, J (C-F)=33.0 Hz), 129.6 (2), 128.3, 127.0 (q, J(C-F)=3.8 Hz), 125.7 (q, J(C-F)=3.8 Hz), 123.4 (q, J(C-F)=272.5 Hz).

MS (70 eV, EI) m/z (%): 294 (60), 292 (100) [M$^+$], 266 (17), 264 (25), 229 (28), 206 (16), 204 (49), 194 (21), 169 (13), 138 (10), 136 (24), 113 (25), 59 (18).

IR (ATR) ṽ (cm$^{-1}$): 3048, 2359, 1743, 1614, 1558, 1485, 1435, 1361, 1323, 1309, 1281, 1241, 1226, 1214, 1167, 1144, 1109, 1097, 1078, 1060, 1042, 1001, 933, 917, 903, 884, 803, 782, 755, 709, 697, 660, 645, 639, 632, 625, 620, 614, 606, 601.

HRMS (EI) for C$_{11}$H$_5$Cl$_2$F$_3$N$_2$ (291.9782): 291.9785.

Synthesis of 4,6-dichloro-5-iodo-pyrimidine (8a)

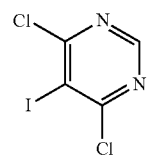

4,6-Dichloropyrimidine 6 (149 mg, 1.0 mmol) in THF (2 mL) was added to a solution of TMPZnCl.LiCl (2) (1.3 M in THF, 0.85 mL, 1.1 mmol) at 25° C. and the reaction mixture was then stirred at this temperature for 45 min according to TP 2. I$_2$ (381 mg, 1.5 mmol) dissolved in dry THF (2 mL) was then dropwise added and the resulting mixture was stirred for 0.5 h. The reaction mixture was quenched with a sat. aq. Na$_2$S$_2$O$_3$ solution (10 mL) and with a sat. aq. NH$_4$Cl solution (20 mL), extracted with diethyl ether (3×50 mL) and dried over anhydrous Na$_2$SO$_4$. After filtration, the solvent was evaporated in vacuo. Purification by flash-chromatography (CH$_2$Cl$_2$/n-pentane, 1:4) furnished compound 8a (227 mg, 83%) as a colourless solid.

m.p.: 134.9-136.5 ° C.

$^1$H NMR (300 MHz, CDCl$_3$) δ: 8.65 (s, 1 H).

$^{13}$C NMR (75 MHz, CDCl$_3$) δ: 166.6, 156.8, 98.9.

MS (70 eV, EI) m/z (%): 274 (100) [M$^+$], 239 (27), 97 (12), 83 (12), 57 (21).

IR (ATR) ṽ (cm$^{-1}$): 2923, 2855, 1900, 1499, 1386, 11341, 1296, 1214, 1080, 1014, 790, 763, 745.

HRMS (EI) for $C_4HCl_2IN_2$ (273.8561): 273.8565.

Synthesis of (4,6-dichloropyrimidin-5-yl)(furan-2-yl)methanone (8b)

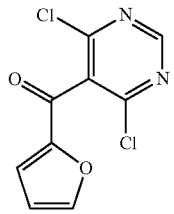 [SMILES: O=C(c1ccco1)c1c(Cl)ncnc1Cl]

4,6-Dichloropyrimidine 6 (149 mg, 1.0 mmol) in THF (2 mL) was added to a solution of TMPZnCl.LiCl (2) (1.3 M in THF, 0.85 mL, 1.1 mmol) at 25° C. and the reaction mixture was then stirred at this temperature for 45 min according to TP 2. CuCN.2LiCl (1.0 M solution in THF, 1.1 mL, 1.1 mmol) was slowly added at −20° C. and the reaction mixture was stirred at the same temperature for 30 min. Then, furan-2-carbonyl chloride (261 mg, 2.0 mmol) was dropwise added at −20° C. and the resulting mixture was allowed to warm up slowly to 25° C. overnight. The reaction mixture was quenched with a sat. aq. NH$_4$Cl solution (30 mL), extracted with diethyl ether (5×30 mL) and dried over anhydrous Na$_2$SO$_4$. After filtration, the solvent was evaporated in vacuo. Purification by flash-chromatography (CH$_2$Cl$_2$/n-pentane 1:1) furnished 8b as a colourless solid (172 mg, 71%).

m.p.: 143.6-145.4° C.

$^1$H NMR (400 MHz, CDCl$_3$) δ: 8.88 (s, 1 H), 7.70 (m, 1 H), 7.28 (m, 1 H), 6.66 (m, 1 H).

$^{13}$C NMR (100 MHz, CDCl$_3$) δ: 175.6, 158.8, 158.4, 150.8, 149.0, 130.9, 121.5, 113.5.

MS (70 eV, EI) m/z (%): 242 (48) [M$^+$], 167 (49), 95 (100), 58 (21), 43 (33).

IR (ATR) ṽ (cm$^{-1}$): 3133, 2969, 2359, 2340, 1738, 1636, 1558, 1540, 1512, 1450, 1403, 1375, 1361, 1297, 1230, 1216, 1168, 1123, 1083, 1032, 956, 904, 888, 878, 815, 789, 781, 746, 738, 668, 626, 615, 609.

HRMS (EI) for $C_9H_4Cl_2N_2O_2$ (241.9650): 241.9653.

Synthesis of 5-allyl-4,6-dichloropyrimidine (8c)

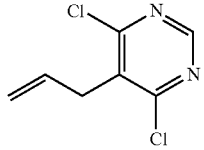

4,6-Dichloropyrimidine 6 (149 mg, 1.0 mmol) in THF (2 mL) was added to a solution of TMPZnCl.LiCl (2) (1.3 M in THF, 0.85 mL, 1.1 mmol) at 25° C. and the reaction mixture was then stirred at this temperature for 45 min according to TP 2. CuCN.2LiCl (1 M in THF; 0.05 mL, 5 mol %) was then slowly added at −20° C. Allyl bromide (242 mg, 2.0 mmol) was then slowly added at −60° C. The resulting mixture was then allowed to warm up slowly to 0° C. for 4 h. The reaction mixture was quenched with a sat. aq. NH$_4$Cl solution (20 mL), extracted with diethyl ether (5×30 mL) and dried over anhydrous Na$_2$SO$_4$. After filtration, the solvent was evaporated in vacuo. Purification by flash-chromatography (CH$_2$Cl$_2$/n-pentane 1:2) furnished 8c as a colourless solid (215 mg, 89%).

$^1$H NMR (300 MHz, CDCl$_3$) δ: 8.64 (s, 1 H), 5.80-5.90 (m, 1 H), 5.09-5.18 (m, 2 H), 3.64 (dt, $^3$J=6.4 Hz, $^4$J=1.4 Hz, 2 H).

$^{13}$C NMR (75 MHz, CDCl$_3$) δ: 162.0, 155.8, 130.9, 130.6, 118.2, 34.0.

MS (70 eV, EI) m/z (%): 188 (70) [M$^+$], 125 (22), 117 (44), 90 (59), 64 (35), 49 (43), 41 (100).

IR (ATR) ṽ (cm$^{-1}$): 2969, 2360, 1739, 1639, 1539, 1513, 1435, 1406, 1375, 1348, 1313, 1290, 1200, 1162, 1129, 1090, 989, 929, 906, 839, 777, 687, 668, 627, 621, 616.

HRMS (EI) for $C_7H_6Cl_2N_2$ (187.9908): 187.9913.

Synthesis of 3,5-dichloro-2-iodopyrazine (11a)

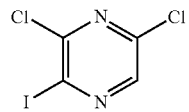

2,6-Dichloropyrazine (9) (149 mg, 1.0 mmol) in THF (2 mL) was added to a solution of TMPZnCl.LiCl (2) (1.3 M in THF, 0.85 mL, 1.1 mmol) at 25° C. and the reaction mixture was then stirred at this temperature for 30 min according to TP 2. I$_2$ (381 mg, 1.5 mmol) dissolved in dry THF (2 mL) was then dropwise added and the resulting mixture was stirred for 0.5 h. The reaction mixture was quenched with a sat. aq. Na$_2$S$_2$O$_3$ solution (10 mL) and with a sat. aq. NH$_4$Cl solution (20 mL), extracted with diethyl ether (3×50 mL) and dried over anhydrous Na$_2$SO$_4$. After filtration, the solvent was evaporated in vacuo. Purification by flash-chromatography (CH$_2$Cl$_2$/n-pentane, 1:2) furnished compound 11a (251 mg, 90%) as a colourless solid.

m.p.: 101.3-103.0° C.

$^1$H-NMR (300 MHz, CDCl$_3$) δ: 8.30 (s, 1 H).

$^{13}$C-NMR (75 MHz, CDCl$_3$) δ: 153.1, 146.9, 142.4, 115.7.

MS (70 eV, EI) m/z (%): 274 (100) [M$^+$], 147 (75), 127 (18), 86 (32), 57 (21), 44 (94).

IR (ATR) ṽ (cm$^{-1}$): 2969, 2633, 2281, 1784, 1738, 1510, 1491, 1379, 1353, 1323, 1274, 1230, 1217, 1205, 1175, 1162, 1143, 1018, 893, 843, 655, 634, 618, 611, 604.

HRMS (EI) for $C_4HCl_2IN_2$ (273.8561): 273.8555.

Synthesis of ethyl 4-(3,5-dichloropyrazin-2-yl)benzoate (11b)

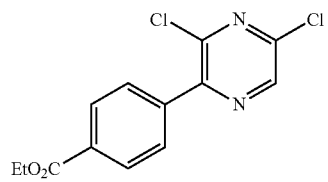 [SMILES: CCOC(=O)c1ccc(-c2ncc(Cl)nc2Cl)cc1]

2,6-Dichloropyrazine (9) (149 mg, 1.0 mmol) in THF (2 mL) was added to a solution of TMPZnCl.LiCl (2) (1.3 M in THF, 0.85 mL, 1.1 mmol) at 25° C. and the reaction mixture was then stirred at this temperature for 30 min according to TP 2. Pd(dba)$_2$ (17 mg, 3 mol %) and P(o-furyl)$_3$ (14 mg, 6 mol %) dissolved in THF (2 mL), followed by the addition of ethyl 4-iodobenzoate (359 mg, 1.3 mmol), were then transferred via cannula to the reaction mixture. The reaction mixture was stirred at 25° C. for 1.5 h. with a sat. aq. NH$_4$Cl solution (20 mL), extracted with diethyl ether (3×50 mL) and dried over anhydrous Na$_2$SO$_4$. After filtration, the solvent was evaporated in vacuo. Purification by flash-chromatography (CH$_2$Cl$_2$/n-pentane, 1:2) furnished compound 11b (251 mg, 87%) as a colourless solid.

m.p.: 88.5-90.0 ° C.

$^1$H-NMR (300 MHz, CDCl$_3$) δ: 8.59 (s, 1 H), 8.14 (d, J=8.6 Hz, 2 H), 7.84 (d, J=8.6 Hz, 2 H), 4.40 (q, J=7.2 Hz, 2 H), 1.40 (t, J=7.0 Hz, 3 H).

$^{13}$C-NMR (75 MHz, CDCl$_3$) δ: 165.8, 150.1, 145.9, 142.0, 139.0, 131.6, 129.4 (2), 61.2, 14.3.

MS (70 eV, EI) m/z (%): 296 (32) [M$^+$], 270 (24), 268 (38), 251 (100), 223 (26).

IR (ATR) $\tilde{v}$ (cm$^{-1}$): 3086, 3005, 2985, 2359, 1966, 1708, 1611, 1569, 1537, 1507, 1482, 1466, 1446, 1423, 1408, 1366, 1310, 1283, 1263, 1190, 1175, 1140, 1131, 1114, 1098, 1028, 1021, 1009, 915, 858, 843, 786, 758, 719, 698, 657, 634, 621, 616, 610, 602.

HRMS (EI) for C$_{13}$H$_{10}$Cl$_2$N$_2$O$_2$ (296.0119): 296.0119.

Synthesis of ethyl 2-((3,5-dichloropyrazin-2-yl)methyl)acrylate (11c)

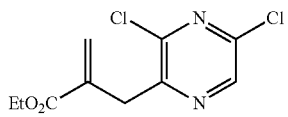 [SMILES: C=C(Cc1ncc(Cl)nc1Cl)C(=O)OCC]

2,6-Dichloropyrazine (9) (149 mg, 1.0 mmol) in THF (2 mL) was added to a solution of TMPZnCl.LiCl (2) (1.3 M in THF, 0.85 mL, 1.1 mmol) at 25° C. and the reaction mixture was then stirred at this temperature for 30 min according to TP 2. After cooling down to −50° C., ethyl 2-(bromomethyl) acrylate (230 mg, 1.2 mmol) and CuCN.2LiCl (1.0 M solution in THF, 5 drops) were added and the resulting mixture was allowed to warm up slowly to −20° C. The reaction mixture was quenched with a sat. aq. NH$_4$Cl solution (20 mL), extracted with diethyl ether (3×50 mL) and dried over anhydrous Na$_2$SO$_4$. After filtration, the solvent was evaporated in vacuo. Purification by flash-chromatography (CH$_2$Cl$_2$/n-pentane, 1:3) furnished compound 11c (187 mg, 72%) as a colourless oil.

$^1$H-NMR (300 MHz, CDCl$_3$) δ: 8.38 (s, 1 H), 6.34 (s, 1 H), 5.56 (s, 1 H), 4.14 (q, J=7.1 Hz, 2 H), 3.92 (s, 2 H), 1.21 (t, J=7.1 Hz, 3 H).

$^{13}$C-NMR (75 MHz, CDCl$_3$) δ: 166.0, 151.5, 146.8, 145.0, 141.5, 136.0, 127.6, 60.9, 36.7, 14.0.

MS (70 eV, EI) m/z (%): 261 (100) [M$^+$-H], 163 (10).

IR (ATR) $\tilde{v}$ (cm$^{-1}$): 2969, 2359, 1738, 1503, 1385, 1342, 1294, 1226, 1215, 1084, 1013, 987, 954, 795, 764, 749, 667, 621, 615, 608, 603.

HRMS (ESI) for C$_{10}$H$_{10}$Cl$_2$N$_2$O$_2$ (260.0119 (M$^+$-H)): 261.0196.

Synthesis of 8-(4-chlorophenyl)-1,3,7-trimethyl-1H-purine-2,6(3H,7H)-dione (14a)

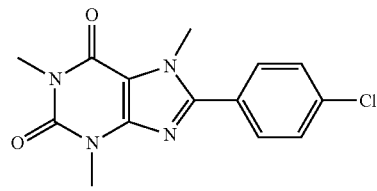 [SMILES: Cn1c(=O)c2c(nc(-c3ccc(Cl)cc3)n2C)n(C)c1=O]

TMPZnCl.LiCl (2) (1.3 M in THF, 0.85 mL, 1.1 mmol) was added to a solution of 1,3,7-trimethyl-1H-purine-2,6(3H, 7H)-dione (12) (194 mg, 1.0 mmol) in THF (2 mL) at 25° C. and the reaction mixture was then stirred at this temperature for max. 5 min. Pd(dba)$_2$ (17 mg, 3 mol %) and P(o-furyl)$_3$ (14 mg, 6 mol %) dissolved in THF (2 mL), and mixed with 1-chloro-4-iodobenzene (310 mg, 1.3 mmol, 1.3 equiv) were then transferred via cannula to the reaction mixture. The resulting mixture was stirred for 1 h at 25° C. The reaction mixture was then quenched with a sat. aq. NH$_4$Cl solution (20 mL), extracted with diethyl ether (3×50 mL) and dried over anhydrous Na$_2$SO$_4$. After filtration, the solvent was evaporated in vacuo. Purification by flash-chromatography (CH$_2$Cl$_2$/ether, 1:1) furnished compound 14a (226 mg, 74%) as a colourless solid.

$^1$H-NMR (300 MHz, CDCl$_3$) δ: 7.62 (d, J=8.5 Hz, 2 H), 7.48 (d, J=8.5 Hz, 2 H), 4.03 (s, 3 H), 3.59 (s, 3 H), 3.39 (s, 3 H).

$^{13}$C-NMR (75 MHz, CDCl$_3$) δ: 155.4, 151.5, 150.7, 148.1, 136.7, 130.4, 129.2, 126.7, 108.6, 33.9, 29.8, 28.0.

MS (70 eV, EI) m/z (%): 304 (100) [M$^+$], 82 (23), 67 (13).

IR (ATR) $\tilde{v}$ (cm$^{-1}$): 2969, 1738, 1694, 1646, 1605, 1569, 1538, 1473, 1454, 1430, 1408, 1374, 1288, 1229, 1216, 1180, 1108, 1090, 1074, 1030, 1008, 977, 835, 803, 759, 749, 739, 730, 708, 685, 671, 650, 645, 639, 632, 625, 620, 614, 606. 601.

HRMS (ESI) for C$_{14}$H$_{13}$ClN$_4$O$_2$ (304.0727): 304.0722.

Synthesis of ethyl 2-((1,3,7-trimethyl-2,6-dioxo-2,3,6,7-tetrahydro-1H-purin-8-yl)methyl)acrylate (14b)

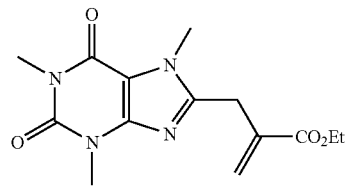 [SMILES: C=C(Cc1nc2c(c(=O)n(C)c(=O)n2C)n1C)C(=O)OCC]

TMPZnCl.LiCl (2) (1.3 M in THF, 0.85 mL, 1.1 mmol) was added to a solution of 1,3,7-trimethyl-1H-purine-2,6(3H, 7H)-dione (12) (194 mg, 1.0 mmol) in THF (2 mL) at 25° C. and the reaction mixture was then stirred at this temperature for max. 5 min. After cooling down to −50 ° C., ethyl 2-(bromomethyl)acrylate (230 mg, 1.2 mmol) and CuCN.2LiCl (1.0 M solution in THF, 5 drops) were added and the resulting mixture was allowed to warm up slowly overnight. The reaction mixture was quenched with a sat. aq. NH$_4$Cl solution (20 mL), extracted with diethyl ether (3×50 mL) and dried over anhydrous $Na_2SO_4$. After filtration, the solvent was evaporated in vacuo. Purification by flash-chromatography ($CH_2Cl_2$/ether, 1:1) furnished compound 14b (211 mg, 69%) as a colourless solid.

$^1$H-NMR (300 MHz, $CDCl_3$) δ: 6.28 (s, 1 H), 5.49 (s, 1 H), 4.14 (q, J=7.1 Hz, 2 H), 3.86 (s, 3 H), 3.70 (s, 2 H), 3.45 (s, 3 H), 3.29 (s, 3 H), 1.21 (t, J=7.1 Hz, 3 H).

$^{13}$C-NMR (75 MHz, $CDCl_3$) δ: 165.7, 155.1, 151.4, 150.8, 147.7, 135.0, 127.3, 107.4, 61.1, 31.8, 29.6, 29.3, 27.7, 14.0.

MS (70 eV, EI) m/z (%): 306 (78) [M$^+$], 260 (28), 232 (100), 219 (11), 67 (13).

IR (ATR) ṽ (cm$^{-1}$): 2998, 2956, 2358, 1719, 1697, 1658, 1548, 1497, 1448, 1426, 1402, 1362, 1340, 1293, 1253, 1215, 1162, 1112, 1033, 978, 960, 939, 894, 858, 831, 812, 759, 743, 718, 693, 663, 641, 630, 602.

HRMS (ESI) for $C_{14}H_{18}N_4O_4$ (306.1328): 306.1320.

Synthesis of ethyl 2',6'-difluoro-3'-nitrobiphenyl-4-carboxylate (17a)

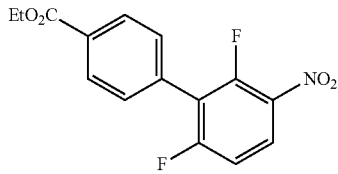 [SMILES: CCOC(=O)c1ccc(-c2c(F)ccc([N+](=O)[O-])c2F)cc1]

2,4-Difluoro-1-nitrobenzene 15 (159 mg, 1.0 mmol) in THF (2 mL) was added to a solution of TMPZnCl.LiCl (2) (1.3 M in THF, 0.85 mL, 1.1 mmol) at 25° C. and the reaction mixture was then stirred at this temperature for 45 min according to TP 2. Pd(dba)$_2$ (17 mg, 3 mol %) and P(o-furyl)$_3$ (14 mg, 6 mol %) dissolved in THF (2 mL), followed by the addition of ethyl 4-iodobenzoate (359 g, 1.3 mmol), were then transferred via cannula at -20° C. The resulting mixture was allowed to warm up slowly to 25° C. overnight. The reaction mixture was then quenchend with a sat. aq. $NH_4Cl$ solution (20 mL), extracted with diethyl ether (3×50 mL) and dried over anhydrous $Na_2SO_4$. After filtration, the solvent was evaporated in vacuo. Purification by flash-chromatography ($CH_2Cl_2$/n-pentane, 1:2) furnished compound 17a (281 mg, 92%) as a colourless solid.

m.p.: 85.0-86.7 ° C.

$^1$H NMR (300 MHz, $CDCl_3$) δ: 8.09-8.18 (m, 1 H), 8.15 (d, J=8.8 Hz, 2 H), 7.51 (d, J=8.8 Hz, 2 H), 7.11-7.18 (m, 1 H), 4.40 (q, J=7.0 Hz, 3 H), 1.40 (d, J=7.0 Hz, 2 H).

$^{13}$C NMR (75 MHz, $CDCl_3$) δ: 165.8, 162.5 (dd, J=6.0 Hz, J=260.1 Hz), 153.7 (dd, J=6.0 Hz, J=260.1 Hz), 131.2 (dd, J=0.5 Hz, J=3.9 Hz), 130.2 (dd, J=1.8 Hz, J=2.0 Hz), 129.7, 126.6 (dd, J=1.8 Hz, J=21.4 Hz), 120.2 (dd, J=28.1 Hz, J=1.8 Hz), 112.1 (dd, J=4.3 Hz, J=24.7 Hz), 61.3, 14.3.

MS (70 eV, EI) m/z (%): 307 (23) [M$^+$], 279 (48), 262 (100), 216 (43), 188 (34), 44 (12).

IR (ATR) ṽ (cm$^{-1}$): 3101, 2969, 2359, 1712, 1621, 1589, 1567, 1535, 1510, 1472, 1404, 1368, 1341, 1304, 1286, 1269, 1215, 1185, 1170, 1148, 1127, 1103, 1070, 1020, 1011, 948, 879, 857, 824, 778, 756, 714, 702, 667, 636, 620, 607, 602.

HRMS (EI) for $C_{15}H_{11}F_2NO_4$ (307.0656): 307.0651.

Synthesis of (2,6-difluoro-3-nitrophenyl)(phenyl)methanone (17b)

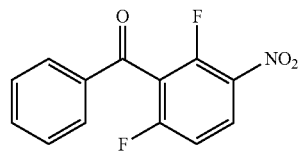 [SMILES: O=C(c1ccccc1)c1c(F)ccc([N+](=O)[O-])c1F]

2,4-Difluoro-1-nitrobenzene 15 (159 mg, 1.0 mmol) in THF (2 mL) was added to a solution of TMPZnCl.LiCl (2) (1.3 M in THF, 0.85 mL, 1.1 mmol) at 25° C. and the reaction mixture was then stirred at this temperature for 45 min according to TP 2. CuCN.2LiCl (1.0 M solution in THF, 1.1 mL, 1.1 mmol) was slowly added at −40 ° C. and the reaction mixture was stirred at the same temperature for 30 min. Then, benzoyl chloride (281 mg, 2.0 mmol) was added dropwise at −40° C. and the resulting mixture was allowed to warm up slowly to 25° C. overnight. The reaction mixture was then quenchend with a sat. aq. $NH_4Cl$ solution (20 mL), extracted with diethyl ether (3×50 mL) and dried over anhydrous $Na_2SO_4$. After filtration, the solvent was evaporated in vacuo. Purification by flash-chromatography ($CH_2Cl_2$/n-pentane, 1:2) furnished compound 17b (221 mg, 84%) as a colourless solid.

m.p.: 75.8-77.2° C.

$^1$H NMR (300 MHz, $CDCl_3$) δ: 7.14-8.31 (m, 7 H).

$^{13}$C NMR (75 MHz, $CDCl_3$) δ: 186.2, 162.2 (dd, J=4.2 Hz, J=262.4 Hz), 153.7 (dd, J=9.0 Hz, J=269.9 Hz), 135.7, 135.1, 133.8, 130.2, 129.6, 129.1, 128.7 (dd, J=2.1 Hz, J=10.9 Hz), 128.5, 119.3 (dd, J=21.9 Hz, J=2.1 Hz).

MS (70 eV, EI) m/z (%): 263 (52) [M$^+$], 105 (100), 33 (77).

IR (ATR) ṽ (cm$^{-1}$): 3100, 1912, 1738, 1675, 1619, 1594, 1530, 1496, 1469, 1450, 1351, 1320, 1311, 1280, 1266, 1217, 1180, 1159, 1128, 1100, 1073, 1034, 1027, 1000, 970, 934, 862, 834, 828, 797, 774, 759, 731, 705, 692, 683, 668, 645, 638, 630, 626, 620; 614, 606, 601.

HRMS (EI) for $C_{13}H_2F_2NO_3$ (263.0394): 263.0393.

Synthesis of 1,3-difluoro-2-iodo-4-nitrobenzene (17c)

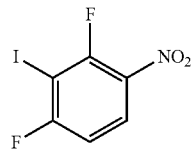

2,4-Difluoro-1-nitrobenzene 15 (159 mg, 1.0 mmol) in THF (2 mL) was added to a solution of TMPZnCl.LiCl (2) (1.3 M in THF, 0.85 mL, 1.1 mmol) at 25° C. and the reaction mixture was then stirred at this temperature for 45 min according to TP 2. I$_2$ (381 mg, 1.5 mmol) dissolved in dry THF (2 mL) was then dropwise added and the resulting mixture was stirred for 0.5 h. The reaction mixture was quenched with a sat. aq. $Na_2S_2O_3$ solution (10 mL) and with a sat. aq.

NH$_4$Cl solution (20 mL), extracted with diethyl ether (3×50 mL) and dried over anhydrous Na$_2$SO$_4$. After filtration, the solvent was evaporated in vacuo. Purification by flash-chromatography (CH$_2$Cl$_2$/n-pentane, 1:1) furnished compound 17c (256 mg, 90%) as a colourless solid.

m.p.: 46.1-47.5° C.

$^1$H NMR (300 MHz, CDCl$_3$) δ: 8.12-8.17 (m, 1 H), 7.04-7.08 (m, 1 H).

$^{13}$C NMR (75 MHz, CDCl$_3$) δ: 165.6 (dd, J=5.0 Hz, J=252.6 Hz), 156.4 (dd, J=6.9 Hz, J=264.1 Hz), 127.7 (dd, J=2.3 Hz, J=10.3 Hz), 111.6 (dd, J=4.2 Hz, J=26.1 Hz), 74.3 (dd, J=29.2 Hz, J=1.9 Hz).

MS (70 eV, El) m/z (%): 285 (100) [M$^+$], 258 (17), 239 (19), 227 (17), 167 (25), 149 (66), 112 (58), 71 (11), 57 (12), 44 (12).

IR (ATR) ṽ (cm$^{-1}$): 3098, 2926, 2855, 2359, 1916, 1739, 1602, 1584, 1529, 1463, 1425, 1336, 1301, 1277, 1218, 1147, 1105, 1011, 860, 827, 751, 698, 669, 621, 616.

HRMS (El) for C$_6$H$_2$F$_2$INO$_2$ (284.9098): 284.9094.

Synthesis of 2-chloro-4-cyclohex-2-enyl-3-nitro-pyridine (20)

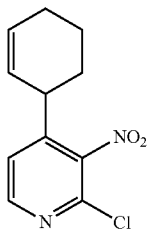

2-Chloro-3-nitropyridine (18) (159 mg, 1.0 mmol) in THF (2 mL) was added to a solution of TMPZnCl.LiCl (2) (1.3 M in THF, 0.85 mL, 1.1 mmol) at 25° C. and the reaction mixture was then stirred at this temperature for 30 min according to TP 2. After cooling down to –50° C., 3-bromo-cyclohexene (192 mg, 1.2 mmol) and CuCN.2LiCl (1.0 M solution in THF, 0.05 mL, 0.05 mmol) were added and the reaction mixture was stirred for 1 h at the same temperature. The reaction mixture was quenched with a sat. aq. NH$_4$Cl solution (20 mL), extracted with diethyl ether (3×50 mL) and dried over anhydrous Na$_2$SO$_4$. After filtration, the solvent was evaporated in vacuo. Purification by flash-chromatography (CH$_2$Cl$_2$/n-pentane, 1:1) furnished 2-chloro-4-cyclohex-2-enyl-3-nitro-pyridine (20) (173 mg, 73%) as a colourless solid.

m.p.: 54.5-55.4 ° C.

$^1$H-NMR (300 MHz, CDCl$_3$) δ: 8.44 (d; $^3$J=5.1 Hz, 1 H), 7.32 (d, $^3$J=5.1 Hz, 1 H), 6.07 (ddd, $^3$J=10.0 Hz, $^3$J=6.1 Hz, $^4$J=3.7 Hz, 1 H), 5.54 (dd, $^3$J=10.0, $^4$J=1.9 Hz, 1 H), 3.46 (m, 1 H), 2.09 (m, 3 H), 1.76 (m, 1 H), 1.64 (m, 1 H), 1.51 (m, 1 H).

$^{13}$C-NMR (75 MHz, CDCl$_3$) δ: 150.2, 150.0, 146.5, 141.8, 131.9, 125.9, 123.3, 37.4, 31.3, 24.7, 20.8.

MS (70 eV, El) m/z (%): 237 (3) [M$^+$-H], 223 (31), 221 (100), 203 (48), 193 (48), 185 (20), 181 (45), 167 (32), 165 (31), 157 (21), 129 (29), 128 (31), 115 (21), 77 (35), 51 (22), 41 (34).

IR (ATR) ṽ (cm$^{-1}$): 2939, 1589, 1539, 1446, 1361, 1347, 1231, 1137, 1041, 973, 918, 890, 855, 845, 757, 723, 691, 616.

HRMS (El) for C$_{11}$H$_{11}$ClN$_2$O$_2$ (237.0431 [M$^+$-H]): 237.0424 [M$^+$-H].

Synthesis of ethyl 2-(6-fluoro-3-methoxy-2-nitrobenzyl)acrylate (23)

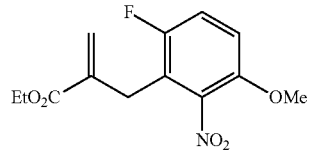 [SMILES: C=C(Cc1c(F)ccc(OC)c1[N+](=O)[O-])C(=O)OCC]

4-Fluoro-1-methoxy-2-nitrobenzene (21) (171 mg, 1.0 mmol) in THF (2 mL) was added to a solution of TMPZnCl.LiCl (2) (1.3 M in THF, 0.85 mL, 1.1 mmol) at 25° C. and the reaction mixture was then stirred at this temperature for 6 h according to TP 2. After cooling down to –50 ° C., ethyl 2-(bromomethyl)acrylate (230 mg, 1.2 mmol) and CuCN.2LiCl (1.0 M solution in THF, 5 drops) were added at –40° C. and the resulting mixture was stirred at the same temperature for 1 h. The reaction mixture was quenched with a sat. aq. NH$_4$Cl solution (20 mL), extracted with diethyl ether (3×50 mL) and dried over anhydrous Na$_2$SO$_4$. After filtration, the solvent was evaporated in vacuo. Purification by flash-chromatography (CH$_2$Cl$_2$/n-pentane, 1:3) furnished compound 23 (189 mg, 67%) as a colourless oil.

$^1$H-NMR (300 MHz, CDCl$_3$) δ: 7.15 (m, 1 H), 8.89-8.93 (m, 1 H), 6.24 (s, 1 H), 5.31 (s, 1 H), 4.19 (q, J=7.1 Hz, 2 H), 3.86 (s, 3 H), 3.63 (bs, 2 H), 1.27 (t, J=7.1 Hz, 3 H).

$^{13}$C-NMR (75 MHz, CDCl$_3$) δ: 165.9, 154.3 (d, J=243.6 Hz), 147.1 (d, J=2.8 Hz), 136.2 (d, J=0.8 Hz), 126.3 (d, J=0.8 Hz), 120.0 (d, J=21.9 Hz), 117.6, 117.3, 111.7 (d, J=8.3 Hz), 61.1, 56.7, 26.9 (d, J=2.9 Hz), 14.1.

MS (70 eV, El) m/z (%): 283 (1) [M$^+$], 237 (100), 209 (88), 192 (58), 166 (20), 149 (21), 133 (16), 121 (13), 99 (11).

IR (ATR) ṽ (cm$^{-1}$): 2969, 2359, 1738, 1503, 1385, 1342, 1294, 1226, 1215, 1084, 1013, 987, 954, 795, 764, 749, 667, 621, 615, 608, 603.

HRMS (ESI) for C$_{13}$H$_{14}$FNO$_5$ (283.0856): 283.0845.

Synthesis of methyl 3-(cyclohex-2-enyl)-5-nitrofuran-2-carboxylate (26)

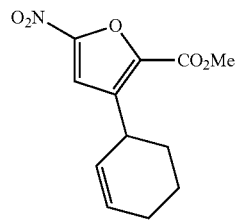 [SMILES: COC(=O)c1oc([N+](=O)[O-])cc1C1C=CCCC1]

Methyl 5-nitrofuran-2-carboxylate (24) (171 mg, 1.0 mmol) in THF (2 mL) was added to a solution of TMPZnCl.LiCl (2) (1.3 M in THF, 0.85 mL, 1.1 mmol) at 25° C. and the reaction mixture was then stirred at this temperature for 30 min according to TP 2. After cooling down to –50° C., 3-bromocyclohexene (209 mg, 1.3 mmol) and CuCN.2LiCl (1.0 M solution in THF, 5 drops) were added and the resulting mixture was stirred for 1 h at this temperature.

The reaction mixture was quenched with a sat. aq. NH₄Cl solution (20 mL), extracted with diethyl ether (3×50 mL) and dried over anhydrous Na₂SO₄. After filtration, the solvent was evaporated in vacuo. Purification by flash-chromatography (CH₂Cl₂/n-pentane, 1:2) furnished compound 26 (179 mg, 72%) as a yellowish oil.

¹H-NMR (400 MHz, CDCl₃) δ: 7.20 (s, 1 H), 5.94 (m, 1 H), 5.56 (m, 1 H), 4.10 (m, 1 H), 3.92 (s, 3 H), 2.07 (m, 3 H), 1.50-1.69 (m, 3 H).

¹³C-NMR (100 MHz, CDCl₃) δ: 157.5, 142.6, 133.9, 130.4, 126.2, 120.1, 52.8, 32.2, 29.0, 24.6, 20.5.

MS (70 eV, El) m/z (%): 252 (2) [M⁺], 234 (100), 217 (55), 146 (10).

IR (ATR) ṽ (cm⁻¹): 2936, 2356, 1729.35, 1629, 1594, 1532, 1502, 1435, 1398, 1338, 1288, 1226, 1206, 1110, 1091, 985, 925, 880, 848, 819, 799, 763, 725, 668, 634, 622.

HRMS (El) for C₁₂H₁₃NO₅ (251.0794): 251.0794.

Synthesis of 2-(3-(trifluoromethyl)phenyl)benzo[b]thiophene-3-carbaldehyde (29a)

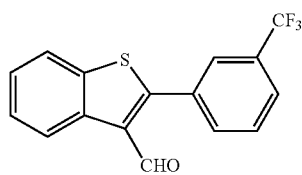 [SMILES: O=Cc1c(-c2cccc(C(F)(F)F)c2)sc2ccccc12]

Benzo[b]thiophene-3-carbaldehyde (27) (162 mg, 1.0 mmol) in THF (2 mL) was added to a solution of TMPZnCl.LiCl (2) (1.3 M in THF, 0.85 mL, 1.1 mmol) at 25° C. and the reaction mixture was then stirred at this temperature for 30 min according to TP 2. Pd(dba)₂ (17 mg, 3 mol %) and P(o-furyl)₃ (14 mg, 6 mol %) dissolved in THF (2 mL), and mixed with 3-iodobenzomethyltrifluoride (354 mg, 1.3 mmol, 1.3 equiv) were then transferred via cannula to the reaction mixture. The resulting mixture was stirred for 1 h at 25° C. The reaction mixture was then quenched with a sat. aq. NH₄Cl solution (20 mL), extracted with diethyl ether (3×50 mL) and dried over anhydrous Na₂SO₄. After filtration, the solvent was evaporated in vacuo. Purification by flash-chromatography (CH₂Cl₂/n-pentane, 1:3) furnished compound 29a (281 mg, 92%) as a colourless solid.

m.p.: 102.8 -104.2° C.

¹H-NMR (400 MHz, CDCl₃) δ: 10.02 (s, 1 H), 8.79 (m, 1 H), 7.45-7.87 (m, 7 H).

¹³C-NMR (100 MHz, CDCl₃) δ: 185.9, 158.0, 138.0, 136.8, 133.7, 132.4, 131.5 (q, J(C-F)=33.0 Hz), 130.7, 129.5, 127.0 (q, J(C-F)=3.8 Hz), 126.6 (q, J(C-F)=3.8 Hz), 126.5, 126.2, 123.5 (q, J(C-F)=272.5 Hz), 121.7.

MS (70 eV, El) m/z (%): 306 (97) [M⁺], 305 (100), 278 (12), 257 (13), 237 (28), 233 (18), 208 (29), 160 (13), 44 (40).

IR (ATR) ṽ (cm⁻¹): 3068, 2866, 2359, 1926, 1745, 1669, 1590, 1520, 1483, 1459, 1438, 1421, 1392, 1351, 1325, 1310, 1288, 1265, 1217, 1178, 1156, 1118, 1097, 1092, 1073, 1051, 1018, 1000, 994, 966, 947, 933, 907, 868, 863, 812, 773, 754, 733, 703, 679, 653, 641, 633, 620, 608, 603.

HRMS (El) for C₁₆H₉F₃OS (306.0326): 306.0326.

Synthesis of 2-(4-chlorophenyl)benzo[b]thiophene-3-carbaldehyde (29b)

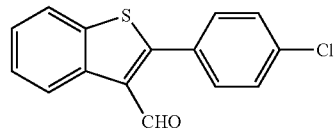 [SMILES: O=Cc1c(-c2ccc(Cl)cc2)sc2ccccc12]

Benzo[b]thiophene-3-carbaldehyde (27) (162 mg, 1.0 mmol) in THF (2 mL) was added to a solution of TMPZnCl.LiCl (2) (1.3 M in THF, 0.85 mL, 1.1 mmol) at 25° C. and the reaction mixture was then stirred at this temperature for 30 min according to TP 2. Pd(dba)₂ (17 mg, 3 mol %) and P(o-furyl)₃ (14 mg, 6 mol %) dissolved in THF (2 mL), and mixed with 1-chloro-4-iodobenzene (310 mg, 1.3 mmol, 1.3 equiv) were then transferred via cannula to the reaction mixture. The resulting mixture was stirred for 2 h at 25° C. The reaction mixture was then quenched with a sat. aq. NH₄Cl solution (20 mL), extracted with diethyl ether (3×50 mL) and dried over anhydrous Na₂SO₄. After filtration, the solvent was evaporated in vacuo. Purification by flash-chromatography (CH₂Cl₂/n-pentane, 1:3) furnished compound 29b (236 mg, 87%) as a colourless solid.

m.p.: 99.7-101.4° C.

¹H-NMR (300 MHz, CDCl₃) δ: 10.02 (s, 1 H), 8.76 (d, J=8.0 Hz, 1 H), 7.83 (d, J=8.0 Hz, 1 H), 7.42-7.54 (m, 6 H).

¹³C-NMR (75 MHz, CDCl₃) δ: 186.2, 158.9, 137.8, 136.9, 136.4, 131.6, 130.3, 130.0, 129.2, 126.4, 126.0, 125.2, 121.6.

MS (70 eV, El) m/z (%): 272 (100) [M⁺], 237 (54), 208 (34), 165 (12), 118 (20), 104 (23).

IR (ATR) ṽ (cm⁻¹): 3054, 2969, 2867, 2362, 1947, 1739, 1671, 1590, 1562, 1517, 1482, 1457, 1431, 1407, 1397, 1346, 1265, 1218, 1187, 1161, 1135, 1109, 1091, 1050, 1020, 1012, 971, 952, 938, 846, 830, 813, 748, 723, 716, 710, 698, 667, 638, 616, 610, 603.

HRMS (El) for C₁₅H₉ClOS (272.0063): 272.0057.

Synthesis of 2-(phenylethynyl)benzo[b]thiophene-3-carbaldehyde (29c)

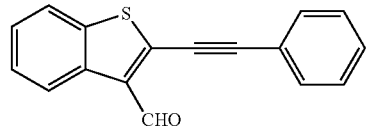 [SMILES: O=Cc1c(C#Cc2ccccc2)sc2ccccc12]

Benzo[b]thiophene-3-carbaldehyde (27) (162 mg, 1.0 mmol) in THF (2 mL) was added to a solution of TMPZnCl.LiCl (2) (1.3 M in THF, 0.85 mL, 1.1 mmol) at 25° C. and the reaction mixture was then stirred at this temperature for 30 min according to TP 2. I₂ (381 mg, 1.5 mmol) dissolved in dry THF (2 mL) was then dropwise added and the resulting mixture was stirred for 0.5 h. To the solution of freshly generated in situ 2-iodobenzo[b]thiophene-3-carbaldehyde, NEt₃ (7 mL), CuI (8 mg, 4 mol %), Pd(dba)₂ (17 mg, 3 mol %) and P(o-furyl)$_3$ (14 mg, 6 mol %) in THF (2 mL) and phenylacetylene (254 mg, 1.5 mol, 1.5 equiv) were successively slowly added. The reaction mixture was stirred at rt for 2 h. The reaction mixture was quenched with a sat. aq. Na$_2$S$_2$O$_3$ solution (10 mL) and with a sat. aq. NH$_4$Cl solution (20 mL), extracted with diethyl ether (3×50 mL) and dried over anhydrous Na$_2$SO$_4$. After filtration, the solvent was evaporated in vacuo. Purification by flash-chromatography (CH$_2$Cl$_2$/n-pentane, 1:2) furnished compound 29c (165 mg, 63%) as a yellowish solid.

m.p.: 104.9-106.5 ° C.

$^1$H-NMR (400 MHz, CDCl$_3$) δ: 10.47 (s, 1 H), 8.69 (m, 1 H), 7.77 (m, 1 H), 7.60 (m, 2 H), 7.38-7.51 (m, 5 H).

$^{13}$C-NMR (100 MHz, CDCl$_3$) δ: 185.6, 138.9, 138.5, 135.9, 135.2, 131.8, 129.8, 128.6, 126.8, 126.5, 124.9, 121.6, 121.3, 102.9, 80.0.

MS (70 eV, EI) m/z (%): 262 (100) [M$^+$], 234 (38), 232 (13), 202 (11), 189 (13).

IR (ATR) $\tilde{v}$ (cm$^{-1}$): 2969, 2832, 2359, 2340, 2203, 1739, 1661, 1587, 1569, 1507, 1481, 1458, 1442, 1427, 1361, 1316, 1293, 1250, 1229, 1216, 1177, 1162, 1141, 1119, 1070, 1059, 1043, 1015, 997, 953, 918, 868, 748, 737, 697, 687, 668, 630, 621, 616, 610.

HRMS (EI) for C$_{17}$H$_{10}$OS (262.0452): 262.0459.

The invention claimed is:

1. The compound 2,2,6,6-Tetramethylpiperide Zinc Chloride Lithium Chloride.

* * * * *